(12) United States Patent
Sandler et al.

(10) Patent No.: US 10,391,016 B2
(45) Date of Patent: Aug. 27, 2019

(54) MACHINE TO HUMAN INTERFACES FOR COMMUNICATION FROM A LOWER EXTREMITY ORTHOTIC

(71) Applicant: Ekso Bionics, Inc., Richmond, CA (US)

(72) Inventors: Reuben Sandler, Berleley, CA (US); Kurt Amundson, Berkeley, CA (US); James Stryker, Mountain View, CA (US); Katherine Strausser, Berkeley, CA (US); Adam Zoss, Berkeley, CA (US); Tim Swift, Clovis, CA (US)

(73) Assignee: Ekso Bionics, Inc., Richmond, CA (US)

( * ) Notice: Subject to any disclaimer, the term of this patent is extended or adjusted under 35 U.S.C. 154(b) by 847 days.

(21) Appl. No.: 14/776,406

(22) PCT Filed: Mar. 12, 2014

(86) PCT No.: PCT/US2014/024244
§ 371 (c)(1),
(2) Date: Sep. 14, 2015

(87) PCT Pub. No.: WO2014/159577
PCT Pub. Date: Oct. 2, 2014

(65) Prior Publication Data
US 2016/0045386 A1    Feb. 18, 2016

Related U.S. Application Data

(60) Provisional application No. 61/781,347, filed on Mar. 14, 2013.

(51) Int. Cl.
*A61H 3/00* (2006.01)
*A61F 5/01* (2006.01)
(Continued)

(52) U.S. Cl.
CPC .............. *A61H 3/00* (2013.01); *A61B 5/1124* (2013.01); *A61B 5/4851* (2013.01);
(Continued)

(58) Field of Classification Search
CPC .............. A61H 3/00; A61H 2201/5061; A61H 2201/5058; A61H 2201/5094;
(Continued)

(56) References Cited

U.S. PATENT DOCUMENTS

| 4,751,917 A | 6/1988 | Ruf |
| 5,679,004 A | 10/1997 | McGowan et al. |

(Continued)

FOREIGN PATENT DOCUMENTS

| EP | 2189136 | 5/2010 |
| JP | 2004008605 | 1/2004 |

(Continued)

*Primary Examiner* — Quang D Thanh
(74) *Attorney, Agent, or Firm* — Diedericks & Whitelaw, PLC

(57) ABSTRACT

An exoskeleton includes a control system which incorporates a feedback system used to establish and communicate orthosis operational information to a physical therapist and/or to an exoskeleton user. The feedback system can take various forms, including employing sensors to establish a feedback ready value and communicating the value through one or more light sources which can be in close proximity to joints of the exoskeleton joints.

26 Claims, 12 Drawing Sheets

(51) Int. Cl.
*A61B 5/11* (2006.01)
*A61B 5/00* (2006.01)

(52) U.S. Cl.
CPC ............ *A61B 5/6811* (2013.01); *A61B 5/742* (2013.01); *A61B 5/7415* (2013.01); *A61B 5/7455* (2013.01); *A61F 5/0102* (2013.01); *A61H 2201/5058* (2013.01); *A61H 2201/5061* (2013.01); *A61H 2201/5094* (2013.01)

(58) Field of Classification Search
CPC ..... A61B 5/7415; A61B 5/742; A61B 5/7455; A61B 5/6811; A61B 5/1124; A61B 5/4851; A61F 5/0102
See application file for complete search history.

(56) References Cited

U.S. PATENT DOCUMENTS

| | | |
|---|---|---|
| 6,447,425 B1 | 9/2002 | Keller et al. |
| 6,778,866 B1 | 8/2004 | Bettwy |
| 6,852,067 B2 | 2/2005 | Limonadi |
| 7,033,281 B2 | 4/2006 | Carnahan et al. |
| 7,662,122 B2 | 2/2010 | Sterling |
| 7,993,291 B2 | 8/2011 | Karkanias et al. |
| 8,025,632 B2 | 9/2011 | Einarsson |
| 8,475,172 B2 | 7/2013 | Lieberman et al. |
| 8,678,979 B2 | 3/2014 | Stark et al. |
| 9,168,195 B2 | 10/2015 | Sankai |
| 2006/0260620 A1 | 11/2006 | Kazerooni et al. |
| 2006/0292533 A1* | 12/2006 | Selod ............ A61H 3/02 434/247 |
| 2008/0071386 A1 | 3/2008 | McBean et al. |
| 2008/0255488 A1* | 10/2008 | Agrawal ........ A63B 21/00181 602/23 |
| 2010/0094188 A1* | 4/2010 | Goffer ............ A61H 3/008 602/23 |
| 2010/0262047 A1 | 10/2010 | Genis |
| 2011/0152736 A1 | 6/2011 | Ng |
| 2012/0017147 A1 | 1/2012 | Mark |
| 2012/0059298 A1 | 3/2012 | Hoffman et al. |
| 2012/0157882 A1 | 6/2012 | Clausen et al. |
| 2012/0165704 A1 | 6/2012 | Kang et al. |
| 2012/0179075 A1 | 7/2012 | Perry et al. |
| 2013/0158445 A1 | 6/2013 | Kazerooni et al. |
| 2013/0197408 A1 | 8/2013 | Goldfarb et al. |

FOREIGN PATENT DOCUMENTS

| | | | |
|---|---|---|---|
| JP | 2008086586 | 4/2008 | |
| JP | 2012115311 | 6/2012 | |
| WO | WO 2012/027336 A1 * | 3/2012 | ............. A61H 1/00 |

* cited by examiner

MACHINE TO HUMAN INTERFACES FOR COMMUNICATION FROM A LOWER EXTREMITY ORTHOTIC

CROSS-REFERENCE TO RELATED APPLICATION

The present application represents a National Stage application of PCT/US2014/024244 entitled "Machine to Human Interfaces for Communication from a Lower Extremity Orthotic" filed Mar. 13, 2014, pending, which claims the benefit of U.S. Provisional Application Ser. No. 61/781,347 filed Mar. 14, 2013 entitled "Machine to Human Interfaces for Communication from a Lower Extremity Orthotic."

BACKGROUND OF THE INVENTION

The present invention relates to a device and method that aids in the rehabilitation and restoration of muscular function in patients with impaired muscular function or control. More particularly, the present invention relates to a device and method suitable for therapeutic use with patients that have impaired neuromuscular/muscular function of the appendages, comprising a motorized system of braces and related control systems that potentiate improved function of the appendages for activities including, but not limited to, walking.

Millions of individuals suffer from either partial or total loss of walking ability. This disabled state can result from traumatic injury, stroke, or other medical conditions that cause disorders that affect muscular control. Regardless of origin, the onset and continuance of walking impairment can result in additional negative physical and/or psychological outcomes for the afflicted individual. In order to improve the health and quality of life of patients with walking impairment, the development of devices that can improve or restore walking function is of significant utility to the medical and therapeutic communities. Beyond walking impairment, there are a range of medical conditions that interfere with muscular control of the appendages, resulting in loss of function and other adverse conditions for the affected individual. The development of devices to improve or restore these functions is also of great interest to the medical and therapeutic communities.

Human exoskeleton devices are being developed in the medical field to restore and rehabilitate proper muscle function for people with disorders that affect muscle control. These exoskeleton devices are a system of motorized braces that can apply forces to the wearer's appendages. In a rehabilitation setting, exoskeletons are typically controlled by a physical therapist who uses one of a plurality of possible input means to command an exoskeleton control system. In turn, the exoskeleton control system actuates the position of the motorized braces, resulting in the application of force to, and typically movement of, the body of the exoskeleton wearer. In some cases, the exoskeleton may also be similarly controlled by input from either the wearer of the exoskeleton or a combination of both wearer and physical therapist input to the exoskeleton control system.

Exoskeleton control systems prescribe and control trajectories in the joints of an exoskeleton. These trajectories can be prescribed as position based, force based, or a combination of both methodologies, such as that seen in an impedance controller. Position based control systems can be modified directly through modification of the prescribed positions. Force based control systems can also be modified directly through modification of the prescribed force profiles.

During a rehabilitation session and/or over the course of rehabilitation, it is highly beneficial for the physical therapist to have the ability to modify the prescribed positions and/or the prescribed force profiles depending on the particular physiology or rehabilitation stage of a patient. It is highly complex and difficult to construct an exoskeleton control interface that enables the full range of modification desired by a physical therapist during rehabilitation. In addition, it is important that the control interface not only allow the full range of modifications that may be desired by a physical therapist, but that the interface with the physical therapist be intuitive to the physical therapist, who may not be highly technically oriented. In some situations, it is similarly beneficial for the wearer of the exoskeleton to be made able to modify exoskeleton trajectories.

Exoskeleton control systems receive intent commands from an exoskeleton operator, who may be either a physical therapist or the exoskeleton wearer, and then performs desired actions accordingly. In order to properly execute these actions, a range of sensors are placed throughout the exoskeleton to sense the exoskeleton state. There are a plurality of possible means by which the operator of an exoskeleton, who may be either a physical therapist or the exoskeleton wearer, may input commands into the exoskeleton control system. However, in order to maximize the rehabilitative benefit of the exoskeleton, it would be of great utility to the exoskeleton operator to receive additional information from the exoskeleton control system, which could communicate information on relative force inputs from the exoskeleton and wearer, deflection from prior trajectory cycles, balance of the exoskeleton, guidance or future positioning information, or any of a host of other parameters.

While the prior art includes references to devices intended to indicate safe ranges of motion or desired motions for passive orthoses, these indicators are generally limited to reminding the person of information (typically joint angle) that they already possess. Furthermore, in these cases, the information is provided intermittently when the device determines interference is warranted. The art has not recognized the need for ways that an exoskeleton or powered orthosis needs to communicate its intentions and motion to the person. The examples known in the art of exoskeletons are limited to discrete indicators of state, equivalent to dashboard indicators on a car; this invention is directed at continual feedback that allows the person to understand and be involved in the motion of the device, which is more analogous to the force feedback provided through the steering wheel on modern cars. The driver is able to feel a portion of the force that the car is applying to the steering so that they perceive the forces acting on the car.

There exists an unmet need to provide a device and method that allows for an exoskeleton to communicate information from an exoskeleton control system to an exoskeleton operator, who may either be a physical therapist or exoskeleton wearer, in such a way that the exoskeleton operator is able to intuitively interpret the information communicated by the exoskeleton and utilize this information to improve the rehabilitative benefit or other uses of the exoskeleton.

SUMMARY OF THE INVENTION

It is an object of the present invention to provide a novel device and method that allows for an exoskeleton control system to communicate information to a physical therapist in an intuitive format, allowing the physical therapist to utilize the information communicated by the exoskeleton control system to maximize the therapeutic benefit of the exoskeleton to the patient, including but not limited to allowing the physical therapist to better modify prescribed exoskeleton trajectories in real-time or for future trajectory cycles, or assess the progression of the rehabilitative state of the patient.

It is another object of the present invention to provide a novel device and method that allows for an exoskeleton control system to communicate information to an exoskeleton wearer in an intuitive format, allowing the exoskeleton wearer to utilize the information communicated by the exoskeleton as either direct or indirect "feedback" allowing for improved information on exoskeleton data such as where exoskeleton work is occurring, where exoskeleton positions are changing, and for fault prediction/warning alarms.

It is an additional object of the present invention to provide a novel device and method that allows for an exoskeleton control system to communicate information to an exoskeleton wearer or a physical therapist in an intuitive format, allowing the exoskeleton to communicate exoskeleton guidance information, such as next-step position, balance centering, or predicted direction of travel.

The invention disclosed herein comprises novel methods of communicating information from an exoskeleton control system to a physical therapist and/or an exoskeleton user, via an exoskeleton feedback system. These exoskeleton-operator communication interface and feedback systems build upon current exoskeleton technology to enable an exoskeleton system to not only restore or enhance human movement, but also restore or enhance human senses. In general, the term feedback system is used to differentiate from the broader set of display technologies: here "feedback system" is used to mean a device that is supplying non-textual information; textual display is used to mean a device that is supplying textual information. Ten various embodiments of feedback systems are disclosed, as well as the sorts of information that the exoskeleton controller may communicate to the person with these feedback devices.

The primary embodiment of this invention comprises of an exoskeleton device equipped with one or more light emitting diodes or other lighting means in close proximity to the exoskeleton joints. The lighting means are connected to the exoskeleton control system and are illuminated proportionally to the torque in the exoskeleton joint. The lighting means could alternately be illuminated proportionally to the assistance level provided by the exoskeleton device. This would provide a physical therapist or the exoskeleton wearer with intuitively placed visual feedback system which communicates the human machine interaction beyond the resultant movement that can be seen directly by the physical therapist or the exoskeleton wearer.

In a secondary embodiment, the visual feedback system comprises of an exoskeleton system including one or more light emitting diodes or other lighting means in close proximity to the exoskeleton wearer connection points. The exoskeleton wearer connection points contain force sensors, which are connected to the exoskeleton control system, that determine the forces exerted between exoskeleton wearer and the exoskeleton at the exoskeleton wearer connection points. The lighting means is connected to the exoskeleton control system and is illuminated proportionally, through modulation of intensity and/or color, to the forces in the connection points as determined force sensors in the exoskeleton wearer connection points. Similarly to the first embodiment, this would allow a physical therapist or the exoskeleton wearer to understand the location of forces transferred between the exoskeleton and the exoskeleton wearer.

In a third embodiment, the visual feedback system comprises of an exoskeleton system including an integral laser pointer. The laser pointer is connected to the exoskeleton structure through actuated means of controlling pan and tilt of beam projection angle. The pan and tilt projection angle actuation means are connected to the exoskeleton control system and controlled such that the laser pointer is aimed at a relevant location to the exoskeleton wearer, such as ideal crutch placement targets, ideal foot placement targets, and next movement target. This would allow the exoskeleton wearer to be intuitively trained in exoskeleton operation as well as allow the exoskeleton wearer to judge more accurately where the exoskeleton movements will take them. It should be noted that a single laser pointer could be designed to overlay a plurality of simultaneous images on the ground by sweeping back outlines on the ground repeatedly, or alternately multiple laser pointers, possibly in multiple colors, might be utilized to project different images.

In a fourth embodiment, the visual feedback system comprises of an exoskeleton system including a plurality of integral lighting means, with the lighting means projecting one or more images/targets with plurality of colored lighting means that sum to white light, as well as glasses worn by the exoskeleton wearer with an optical filter that removes one of the colors projected, making the image/target a visible colored light to the exoskeleton wearer and simultaneously making the image/target a subtle white light to people who are not wearing glasses with optical filters. The lighting means are connected to the exoskeleton structure through actuated means of controlling pan and tilt of lighting means projection. The pan and tilt projection angle actuation means are connected to the exoskeleton control system and controlled such that the laser pointer is aimed at a relevant location to the user such as ideal crutch placement targets, ideal foot placement targets, and next movement target. This embodiment has the strong advantage of allowing the placement targets to be used in public without bystanders noticing.

In a fifth embodiment, the visual feedback system comprises of glasses worn by the exoskeleton wearer with an integrated display system and a camera system, with the glasses displaying placement targets that result in a "heads-up display" to the exoskeleton wearer. The glasses and the cameras are in communication with the exoskeleton control system, and the exoskeleton control system determines the position of the exoskeleton through the plurality of sensors integral to the exoskeleton system that determine exoskeleton pose, while the position of the glasses relative to the exoskeleton system is determined by comparing inertial sensors mounted within the exoskeleton system and inertial sensors mounted within the glasses with integral displays. In this embodiment, the glasses constitute a feedback system in the sense that they are displaying non-textual information, in this case geometries overlaid onto the terrain.

A sixth embodiment of this invention comprises of a method and device mounted upon an exoskeleton or the exoskeleton wearer that transmits information from the exoskeleton control system to the exoskeleton wearer that provides feedback on the center of pressure of the exoskeleton device and wearer. Knowledge of the center of pressure is used by a person to feel when they are balanced over their feet. For users without sensation of pressure in their feet, however, this information must be presented in other methods. Multiple methods of feedback for the center of pressure are possible. A preferred method is to use tactile feedback at an area where the user is able to feel and process that information. One embodiment of center of pressure feedback comprises of a wheel that is attached to the exoskeleton or another structure worn by the exoskeleton wearer. The wheel moves in a plane parallel to the exoskeleton wearer's body to indicate center of pressure motion. The wheel can also be actuated to move in and out providing a varying level of pressure. This the pressure can indicate the speed of the center of pressure, the deviation from ideal, or the difference between the center of pressure and the center of mass. In some embodiments, many such wheels are in contact with the user so that many different the values can be displayed. In some embodiments, the wheel comprises of a ball and drive by the exoskeleton to move in two dimensions (X-Y) and to push with a varying level of the force, producing a three dimensional display capable of displaying information such as, but not limited to, a mapping of the exoskeleton wearer's center of pressure in the forward and lateral axis, as well as the exoskeleton user's vertical force.

In a seventh embodiment, the center of pressure tactile feedback system comprises of vibratory or other tactile motors that are placed on the exoskeleton wearer's body. The motors are in communication with the exoskeleton control system and apply feedback to the exoskeleton wearer by imparting a pushing feel or a sweep to the direction where the exoskeleton wearer should move. The amplitude of the vibration may indicate information such as the desired speed or degree of motion needed. The vibratory feedback could be given on the torso, arms, neck, or head as is appropriate for the feedback and the exoskeleton wearer's level of injury/impairment. These methods may be combined. One embodiment includes the tactile actuators on the aims of the exoskeleton wearer that are activated to mimic a push left or right as a physical therapist would give during gait training. Likewise, in another embodiment the actuators on the chest and back (or front and back of shoulders) of the exoskeleton wearer mimic a push forwards or backwards as would be given by a physical therapist. In some embodiments, arrays of vibration motors may be used to produce relative signals across the exoskeleton wearer's body.

In an eighth embodiment, the center of pressure feedback system comprises a temperature grid connected to the exoskeleton wearer that is in communication with the exoskeleton control system. The temperature grid conveys information to the exoskeleton wearer by means of inducing sensations of temperature. One embodiment is comprised of a heat grid over the tongue of the exoskeleton wearer. In this embodiment, the surface of the tongue of the exoskeleton wearer is mapped to the base of the feet of the exoskeleton wearer. The center of pressure of the exoskeleton wearer and exoskeleton device is then indicated by heating a node in the same position of the grid as the center of pressure over the foot. The degree of the temperature represents the force at the foot.

In a ninth embodiment, the center of pressure feedback system is comprised of an auditory device mounted upon the exoskeleton or the exoskeleton wearer that conveys information from the exoskeleton control system to the exoskeleton wearer by sound. The auditory device is comprised of an array of speakers, and the device indicates to the exoskeleton wearer in the direction and magnitude of deviation from the center of pressure. As the exoskeleton wearer shifts left, the speakers would generate increasingly louder sound on left of the exoskeleton wearer. In one embodiment, the speaker array may simply be comprised of two speakers that are used to give side to side or front to back information in this manner. In another embodiment, the addition of more speakers to the speaker array results in the ability for more precise position information can be transmitted from the exoskeleton control system to the exoskeleton wearer. In another embodiment, one or more the speakers with a variety of tones could be used to indicate to the exoskeleton wearer in the direction and magnitude of deviation from center of pressure. In yet another embodiment, one or more of the speakers are used to continuously vary frequency as a function of lateral position so as to convey center of pressure information to the exoskeleton wearer.

A tenth embodiment of this invention comprises a device attached to a walk aid attached to the exoskeleton wearer that conveys information from the exoskeleton control system to the exoskeleton wearer that provides feedback and guidance to the exoskeleton wearer in regards to the use of the walk aid. In an embodiment, the walk aid comprises a crutch held in each hand of the exoskeleton wearer. The crutch handles are equipped with a vibratory motor that is controlled by the exoskeleton control system. During the walking process, as the exoskeleton wearer shifts their weight, the crutch handle provides vibratory feedback as to where and to what extent the exoskeleton wearer should shift weight. This device is helpful to ensure that the exoskeleton wearer is balanced over their feet rather than relying overly on the walk aid for balance. These methods of feedback used for giving the exoskeleton wearer information about center of pressure can also be used to give the exoskeleton wearer information about their overall positioning, such as the location of their hip over the stance foot or their forward and lateral lean. These feedback mechanisms could indicate a need to shift forward/backward or left/right as necessary to achieve a desired orientation. In another embodiment, the feedback mechanism in the crutch handle is electrostatic haptic or any other haptic feedback mechanism.

Each exoskeleton feedback system comprises an algorithm that converts an exoskeleton control system's data into a "feedback ready" format suitable for communication to an exoskeleton operator, who might be either a physical therapist or the exoskeleton wearer, as well as a method of continuously communicating this "feedback ready" exoskeleton data to an exoskeleton operator. "Feedback ready" conversion algorithms have been developed that enable communication of exoskeleton sensor information, communication of exoskeleton state information, communication of current exoskeleton actions, communication of planned exoskeleton actions, communication of performance feedback/training, and communication of exoskeleton control mode changes. Methods of communication from an exoskeleton to an exoskeleton operator have been developed using visual, haptic, auditory and thermal based human sensory pathways.

Various embodiments were developed to convert exoskeleton data into a "feedback ready" format suitable for communication to an exoskeleton operator. These concepts were evaluated based upon the utility of the information communicated to the exoskeleton operator. The first set of "feedback ready" algorithms utilize information directly from an exoskeleton's various integral sensors that collect data on the exoskeleton state, including but not limited to joint angles and joint torques.

Algorithms that calculate current exoskeleton joint torque relative to the maximum available exoskeleton joint torque have been identified as important novel "feedback ready" triggers to communicate to an exoskeleton operator. These algorithms and the sensors required are readily apparent to a person skilled in the art of exoskeleton design. When joint torque information is communicated to an exoskeleton wearer, an exoskeleton wearer is given a sense which is a corollary to a human's muscle strain sense. This information enables the wearer to better understand an exoskeleton's limits in the same way a person has an understanding of the limits of their own body. This understanding gives the exoskeleton wearer greater confidence when pushing an exoskeleton device near torque limits and the ability to understand where the limits are.

Concepts have also been developed that are variations on joint torque algorithms. One of these other novel "feedback ready" triggers is the expected joint torque minus the actual joint torque provided. The expected joint torque can be approximately calculated based on the exoskeleton wearer's weight and exoskeleton device pose; methods of making this calculation are readily apparent to a person skilled in the art of exoskeleton design. When communicated to the exoskeleton wearer, this expected minus actual torque information provides the exoskeleton wearer with the ability to immediately sense obstacles that are impeding the exoskeleton's movement. Primarily an object on which the exoskeleton is caught can be sensed and enable the exoskeleton wearer to change course rather than build up torque until the exoskeleton bursts free potentially resulting in damage to the exoskeleton or injury to the exoskeleton wearer.

Another novel "feedback ready" trigger related to joint torque is the interaction forces between the exoskeleton and the exoskeleton operator. This force can be measured using common strain gauges or pressure sensors at human-exoskeleton interface points. Communication of this information to the exoskeleton operator enables similar advantages to that of directly communicating joint torque.

Another novel "feedback ready" trigger related to joint torque is the assistance level provided by the device when a device is used in rehabilitative training. Calculation of assistance level is a function of the interaction forces between the exoskeleton and the exoskeleton wearer and is readily apparent to a person skilled in the art of exoskeleton design. This assistance level enables a physical therapist or a rehabilitation patient to understand how much work the machine is doing and how much work the patient is doing. This gives the physical therapist and the patient the target of minimizing the assistance level to maximize rehabilitative benefit. This is especially applicable in rehabilitative gait training for muscle disorders in which the goal is to improve function when the patient is not using the exoskeleton; in this setting this trigger gives the exoskeleton wearer direct feedback as to how much the exoskeleton is modifying their movements and therefore an idea of what their movements would be like without the assistance of an exoskeleton.

If this joint torque based information is communicated to a physical therapist using an exoskeleton device in a rehabilitation setting, it will give the physical therapist an improved understanding of the exoskeleton's effect on the patient. This understanding will enable the physical therapist to make better decisions about a patient's progression and the exoskeleton device settings required for maximum rehabilitative benefit.

Another class of "feedback ready" triggers is based on the exoskeleton and the exoskeleton wearer pose information such as center of pressure location, center of gravity location, and relative exoskeleton segment positions. When used with sensory deficient patients, such as spinal cord injury patients, these triggers attempt to replace the exoskeleton wearer's kinesthetic or somatosensory sense to restore proper proprioception. These embodiments include the positions of the joints relative to each other, which can enable the exoskeleton wearer to understand their position in space more accurately.

In an exoskeleton, center of pressure can be calculated using force or pressure sensors located under the feet of the exoskeleton wearer or exoskeleton device (in the case of an exoskeleton with feet). Center of mass can be calculated using joint angle sensors, the exoskeleton, and the exoskeleton wearer's segment weights. In order to improve the accuracy of these the calculations, the joint angles should be corrected based on the flex of the exoskeleton structure using strain gauges embedded within the exoskeleton structure. Relative exoskeleton segment positions can also be calculated using joint angles, segment lengths and flex corrections.

One novel "feedback ready" trigger in the center of pressure class is the relative position of the center of pressure and center of mass of the exoskeleton and exoskeleton wearer system. This "feedback ready" trigger signifies a direction in which the system is falling and can also be used to indicate the speed of the fall by the distance between the center of pressure and the center of mass. This enables the exoskeleton wearer to directly sense their dynamic stability, which, in an able-bodied individual, is communicated via a combination of their somatosensory sense on their feet and their kinesthetic sense in their lower body.

Another novel "feedback ready" trigger useful with a lower body exoskeletons is the height of each foot from the ground. This trigger acts to restore an exoskeleton wearer's kinesthetic sense. This feedback can be sensed in a variety of manners which are evident to those skilled in the art. One embodiment utilizes proximity sensors, such as sonar emitters and receivers, to calculate the distance to the ground in conjunction with pressure sensors to determine contact. Alternate embodiments may include cameras or laser distance measurements.

Another novel "feedback ready" trigger useful with lower body exoskeletons is the distance from the front of each foot to the closest obstacle. This trigger allows an exoskeleton wearer to sense if it is safe to proceed with a given action. The information fed back to the exoskeleton wearer may include the distance to the obstacle or simply the presence of an obstacle in a given range of the path.

Another novel "feedback ready" trigger useful with lower body exoskeletons is the predicted end effector positions of a selected action. This trigger both provides an exoskeleton wearer with information about an action about to be performed, but also a training target to aim for in order to complete the action. In one embodiment of this method, a visual display, either by a projected point or a heads-up display, informs the exoskeleton wearer of the end position of their foot after the action is performed. In an alternate embodiment, the visual display may indicate where to put a crutch or other walk aid in order to prepare for a step.

Another class of "feedback ready" triggers communicates the control system parameters including current actions, planned actions, and control changes to the exoskeleton wearer. These triggers provide the exoskeleton wearer with an improved understanding of the status of the exoskeleton control system so that the exoskeleton wearer is always aware of exoskeleton actions before they are carried out. These triggers need to be communicated in a non-impeding fashion. This communication of parameter changes or actions also provides the exoskeleton wearer the opportunity to confirm or acknowledge the changes if necessary.

Additional "feedback ready" triggers were conceptualized, including hand to walking aid force vectors, walking aid to ground forces, torso forward and back angle, torso side-to-side angle, joint angles, compass heading, mode change requests, mode change confirmations, action initiation, action completion, alerts to unstable positions, and conditional based on functions of individual triggers.

A number of novel feedback systems were also developed using the feedback triggers described above in conjunction with novel means of providing feedback to an exoskeleton wearer's visual, haptic, auditory and thermal sensory pathways. The following is a description of these specific embodiments of the present invention, including the required constituent sensors, controls, and output interfaces as components of these devices in connection with exoskeleton control.

DETAILED DESCRIPTION OF THE INVENTION

The present invention is used in conjunction with a powered orthotic device that provides for walking motion for the wearer. A powered exoskeleton is one example of such a powered orthotic device. In a rehabilitation setting, powered exoskeletons are controlled by a physical therapist who uses one of a plurality of possible input means to command an exoskeleton control system. In turn, the exoskeleton control system actuates the position of the motorized braces, resulting in the application of force to, and often movement of, the body of the exoskeleton wearer.

Figure 1:
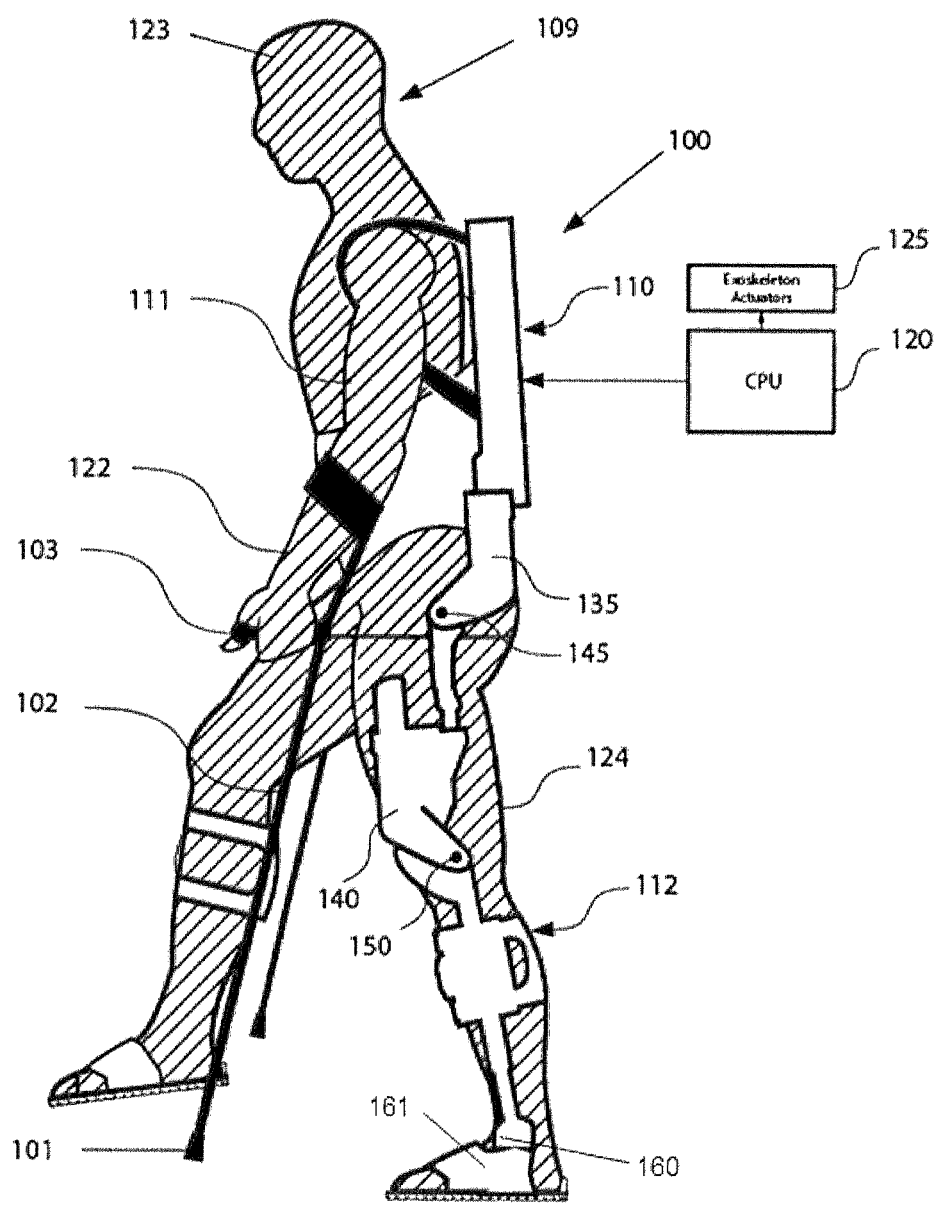
FIG. 1 is a schematic side view of a handicapped individual coupled to an ambulatory exoskeleton.

With reference to FIG. 1, an exoskeleton 100 having a trunk portion 110 and lower leg supports 112 is used in combination with a crutch 102, including a lower, ground engaging tip 101 and a handle 103, by a patient or wearer 109 to walk. The wearer 109 is shown to have an upper arm 111, a lower arm (forearm) 122, a head 123 and lower limbs 124. In a manner known in the art, trunk portion 110 is configurable to be coupled to an upper body (not separately labeled) of the wearer 109, the leg supports 112 are configurable to be coupled to the lower limbs 124 of the wearer 109, foot supports 161 are configurable to be coupled to the feet of wearer 109 and linked to the ankle joint 160, and actuators, generically indicated at 125 but actually interposed between portions of the leg supports 112 as well as between the leg supports 112 and trunk portion 110 in a manner widely known in the art, for shifting of the leg supports 112 relative to the trunk portion 110 to enable movement of the lower limbs 124 of the wearer 109. In some embodiments, trunk portion 110 may be quite small and comprise a pelvic link wrapping around the pelvis of wearer 109. In the example shown in FIG. 1, the exoskeleton actuators 125 are specifically shown as a hip actuator 135 which is used to move hip joint 145 in flexion and extension, and as knee actuator 140 which is used to move knee joint 150 in flexion and extension. The exoskeleton actuators 125 are controlled by CPU 120, with CPU 120 being a constituent of an exoskeleton control system, in a plurality of ways known to one skilled in the art of exoskeleton control. Although not shown in FIG. 1, various sensors in communication with CPU 120 are provided so that CPU 120 may monitor the orientation of the device. Such sensors may include without restriction encoders, potentiometers, accelerometer, and gyroscopes. As the particular structure of the exoskeleton can take various forms, is known in the art and is not part of the present invention, it will not be detailed further herein.

Exoskeleton control systems prescribe and control trajectories in the joints of an exoskeleton. These trajectories can be prescribed as position based, force based, or a combination of both methodologies, such as that seen in an impedance controller. Position based control systems can be modified directly through modification of the prescribed positions. Force based control systems can also be modified directly through modification of the prescribed force profiles. Since the concepts presented here apply equally to position, force, and hybrid "impedance" based control strategies, the positions and/or forces prescribed by an exoskeleton control system may be referred to in this disclosure as the exoskeleton trajectories.

The primary embodiment of this invention comprises of an exoskeleton device equipped with one or more light emitting diodes or other lighting means in close proximity to the exoskeleton joints. The lighting means is connected to the exoskeleton control system and is illuminated proportionally to the torque in the exoskeleton joint. The lighting means could alternately be illuminated proportionally to the assistance level provided by the exoskeleton device. This would provide a physical therapist or the exoskeleton wearer with intuitively placed visual feedback system which communicates the human machine interaction beyond the resultant movement that can be seen directly by the physical therapist or the exoskeleton wearer.

In some embodiments, the intensity of the light might vary in relation to the signal strength, with signal strength as measured by either internal exoskeleton sensors of force sensors on the exoskeleton wearer, and with this signal strength interpreted by the exoskeleton control system and relayed to the lighting means. In another embodiment, the light blinking frequency would change in relation to signal strength. In another embodiment, an array of lights would be used, with the number and position of lights illuminated being relative to the signal strength. In another embodiment, the color of the lights would be modulated relative to signal strength. Other embodiments of lighting feedback are possible, as known to one skilled in the art. Multiple types of sensors could be used to measure various exoskeleton or exoskeleton wearer parameters, and each of these may be reported in the various lighting formats. These multiple formats and parameter feedback types might be combined as preferred.

Figure 2:
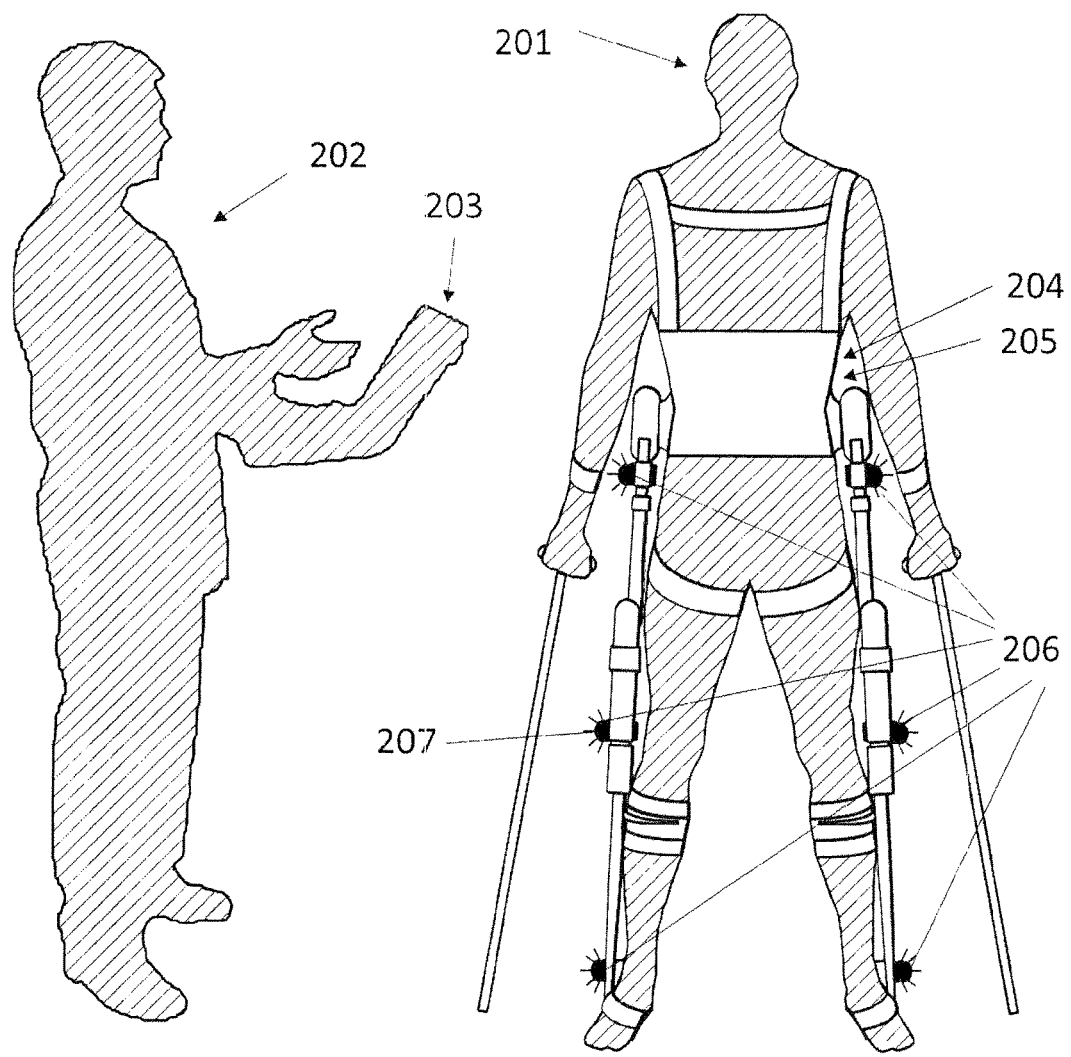
FIG. 2 is a drawing representing a first embodiment that shows an ambulatory exoskeleton with integral joint lights, as well as a physical therapist and exoskeleton wearer that receive visual feedback from the integral joint lights.

With reference to FIG. 2, patient 201 is wearing exoskeleton 204, which is controlled by exoskeleton control system 205. Physical therapist 202 is monitoring the performance of exoskeleton 204 and patient 201 in a rehabilitation setting, during which time physical therapist 202 may issue commands to exoskeleton control system 205 through control system input means 203. While input means 203 is shown here as a computer, this is simply an illustrative example. As input devices are not a particular object of this invention, input means 203 could be any number of devices, including, without limitation, a keypad, voice commands, handles integral to exoskeleton 204, etc. Integral joint lights 206 are illuminated in response to a signal from exoskeleton control system 205, with this signal related to exoskeleton 204 state parameters, in this case exoskeleton joint torque at each exoskeleton joint, causing integral joint lights 206 to increase in illumination intensity as joint torque at each location increases, as calculated by exoskeleton control system 205. Both physical therapist 202 and exoskeleton wearer 201 see the illumination from integral joint lights 206, allowing physical therapist 202 and exoskeleton wearer 201 to have improved understanding of the forces exerted in this exoskeleton state.

In one example of the primary embodiment, if a physical therapist wanted to modify the gait cycle of an ambulatory exoskeleton in response to the progression of a patient over the course of therapy, it is helpful to physical therapist to know how much force was being applied by the patient at each joint relative to the forces exerted by the exoskeleton over a cyclical motion such as walking. As the patient progresses over the course of treatment, the patient will exert more force relative to the exoskeleton at each joint. However, the movement of the exoskeleton will look the same.

The addition of integral lighting means that provide illumination proportionate to the forces exerted by the exoskeleton at each joint may be used as an indirect reporting means to the forces exerted by the patient—as patient and exoskeleton forces sum over a particular movement. In a highly simplified example, the physical therapist might monitor the illumination at the left knee 207 in order to monitor how much joint torque was being exerted at the left knee by the exoskeleton, and thus gain insight as to how much force the patient was able to exert at this left knee at various points over movement cycles and the course of treatment. This information could then be used by the physical therapist to modify exoskeleton trajectories for improved rehabilitative benefit to the patient.

In a second embodiment, the visual feedback system comprises of an exoskeleton system including one or more light emitting diodes or other lighting means in close proximity to the exoskeleton wearer connection points. The exoskeleton wearer connection points contain force sensors, which are connected to the exoskeleton control system, that determine the forces exerted between exoskeleton wearer and the exoskeleton at the exoskeleton wearer connection points. The lighting means is connected the exoskeleton control system and is illuminated proportionally, through modulation of intensity and color, to the forces in the connection points as determined force sensors in the exoskeleton wearer connection points. Similar to the first embodiment, this would allow a physical therapist or the exoskeleton wearer to understand the location of forces transferred between the exoskeleton and the exoskeleton wearer.

Figure 3:
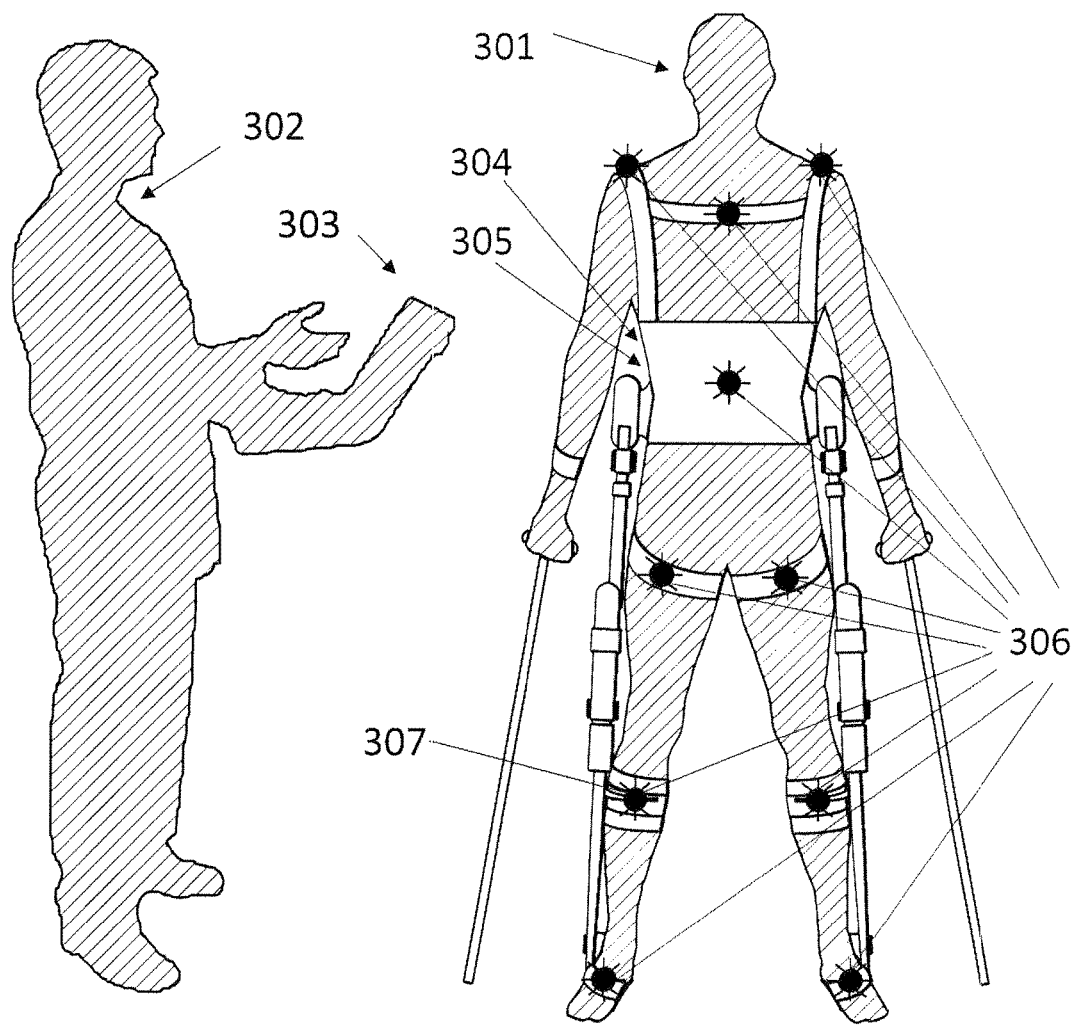
FIG. 3 is a drawing representing a second embodiment that shows an ambulatory exoskeleton with integral exoskeleton-wearer interface point lights, as well as a physical therapist and exoskeleton wearer that receive visual feedback from the integral exoskeleton-wearer interface point lights.

With reference to FIG. 3, patient 301 is wearing exoskeleton 304, which is controlled by exoskeleton control system 305. Physical therapist 302 is monitoring the performance of exoskeleton 304 and patient 301 in a rehabilitation setting, during which time physical therapist 302 may issue commands to exoskeleton control system 305 through control system input means 303. Integral interface point lights 306 are illuminated in response to a signal from force sensors on exoskeleton structure located between exoskeleton 304 and patient 301 at the site of each integral interface point light 306, with the force sensors in communication with exoskeleton control system 305, with this signal indicating the forces exerted between exoskeleton 304 and patient 301, causing integral interface point lights 306 to increase in illumination intensity as force at each location increases. Both physical therapist 302 and exoskeleton wearer 301 see the illumination from integral interface point lights 306, allowing physical therapist 302 and exoskeleton wearer 301 to have improved understanding of the forces exerted by exoskeleton wearer in this exoskeleton state.

In one example of the second embodiment, if a physical therapist wanted to modify the gait cycle of an ambulatory exoskeleton in response to the progression of a patient over the course of therapy, it is helpful to physical therapist to know how much force was being applied by the patient at each joint relative to the forces exerted by the exoskeleton over a cyclical motion such as walking. As the patient progresses over the course of treatment, the patient will exert more force relative to the exoskeleton during various movements. However, the movement of the exoskeleton will look the same. The addition of integral interface point lighting means that provides illumination proportionate to the forces exerted by the patient at one or more exoskeleton-patient interface points allows the physical therapist, or the patient, to receive visual information showing the forces exerted between the exoskeleton and the patient. In a highly simplified example, the physical therapist might monitor the illumination at the left shank coupling 307 in order to monitor how much force torque was being exerted at the left shank coupling, and thus gain insight as to how much force the patient was able to exert at this left shank coupling at various points over movement cycles and the course of treatment. This information could then be used by the physical therapist to modify exoskeleton trajectories for improved rehabilitative benefit to the patient.

Both of the first two embodiments have applications in rehabilitative settings. The novel visual feedback provides the physical therapist with intuitively placed feedback describing the interactions between the exoskeleton and the user which allows the physical therapist to improve the quality of the rehabilitation therapy. This feedback becomes especially important when the physical therapist is provided with control for the device assistance level; this feedback will enable a physical therapist to set the assistance level much more intelligently. Of particular utility to a physical therapist in determining how much relative force exoskeleton and exoskeleton user are exerting over a specific movement is a combination of the first embodiment and the second embodiment, allowing for feedback on both exoskeleton joint torque and exoskeleton-exoskeleton wearer interface force.

In a third embodiment, the visual feedback system comprises of an exoskeleton system including an integral laser pointer. The laser pointer connected to the exoskeleton structure through actuated means of controlling pan and tilt of beam projection angle. The pan and tilt projection angle actuation means connected to the exoskeleton control system and controlled such that the laser pointer is aimed at relevant location to the exoskeleton wearer such as ideal crutch placement targets, ideal foot placement targets, and next movement target. This would allow the exoskeleton wearer to be intuitively trained in exoskeleton operation as well as allow the exoskeleton wearer to judge more accurately where the exoskeleton movements will take them. It should be noted that a single laser pointer could be designed to overlay a plurality of simultaneous images on the ground by sweeping back outlines on the ground repeatedly, or alternately multiple laser pointers, possibly in multiple colors, might be utilized to project different images. In another embodiment, multiple laser pointers sweeping could project duplicate images at the same site, allowing for objects such as a crutch to get in the way of one laser projection without blocking target placement on the ground and disrupting utility to the patient.

Figure 4:
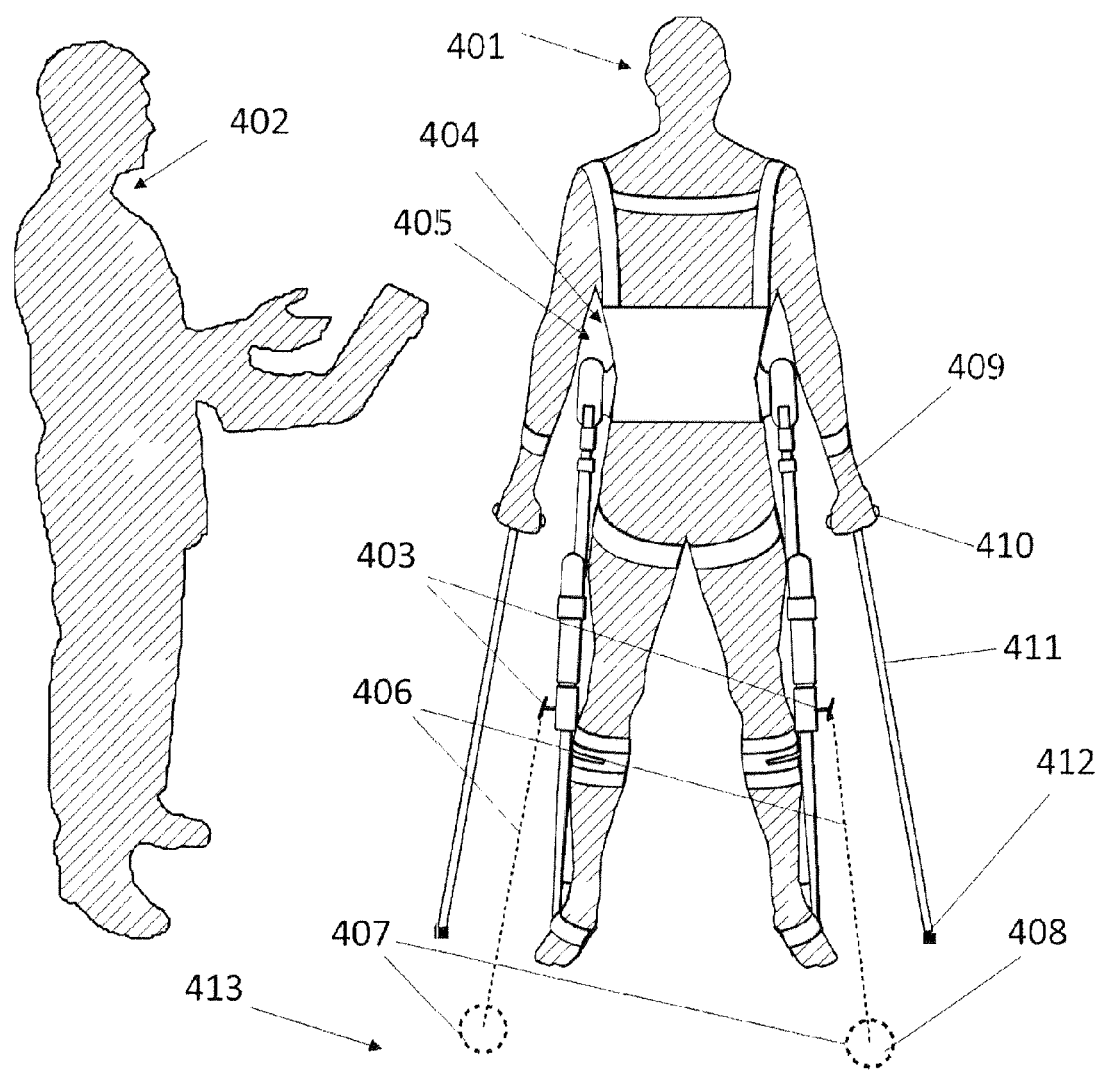
FIG. 4 is a drawing representing a third embodiment that shows an ambulatory exoskeleton with an integral pan/tilt controlled laser pointer, as well as a physical therapist and an exoskeleton wearer that receives visual feedback from the laser pointer, specifically including crutch placement information.

With reference to FIG. 4, patient 401 is wearing exoskeleton 404, which is controlled by exoskeleton control system 405. Physical therapist 402 is monitoring the performance of exoskeleton 404 and patient 401 in a rehabilitation setting. Integral laser pointer connected to articulated means controlling pan and tilt 403 is mounted on the structure of exoskeleton 404. Integral laser pointer 404 projects laser beam 406 which projects crutch placement targets 407 on support surface 413. Patient 401 sees crutch placement targets 407 on support surface 413, allowing for better understanding of where to place crutches. Specifically, patient 401 uses hand 409 to grip crutch handle 410 to guide crutch 411, which has ground interacting tip 412, in such a way as to place ground interacting tip 412 upon specific crutch placement target 408. Physical therapist 402 observes the process and gains better understanding patient 401's skill with use of the exoskeleton and rehabilitative state, allowing for physical therapist 402 to improve the rehabilitative process for patient 401. There are, of course, many other types of gait aid besides a crutch, such as walkers and canes, and a crutch is used here as an exemplary embodiment. It will be apparent to one skilled in the art of exoskeleton design that such a laser pointer device is workable with any such gait aid.

In one example of the third embodiment, a physical therapist is using an exoskeleton in rehabilitation with a new patient who has no previous experience with exoskeleton therapy. The patient is unfamiliar with various aspects of exoskeleton operation and crutch use. The addition of crutch placement targets projected by the integral laser pointers allows for the patient to more quickly become familiar with crutch placement, shortening the time spent by the learning to use the exoskeleton system, allowing for more rapid use in rehabilitation and greater rehabilitative benefit.

In a fourth embodiment, the visual feedback system comprises of an exoskeleton system including a plurality of integral lighting means, with the lighting means projecting one or more images/targets with plurality of colored lighting means that sum to white light, as well as glasses worn by the exoskeleton wearer with an optical filter that removes one of the colors projected, making the image/target a visible colored light to the exoskeleton wearer and simultaneously a subtle white light to people who are not wearing glasses with optical filters. The lighting means is connected to the exoskeleton structure through actuated means of controlling pan and tilt of lighting means projection. The pan and tilt projection angle actuation means connected to exoskeleton control system and controlled such that the projection means is aimed at relevant locations to the user such as ideal crutch placement targets, ideal foot placement targets, and next movement target. This embodiment has the strong advantage of allowing the placement targets to be used in public without bystanders noticing.

Figure 5:
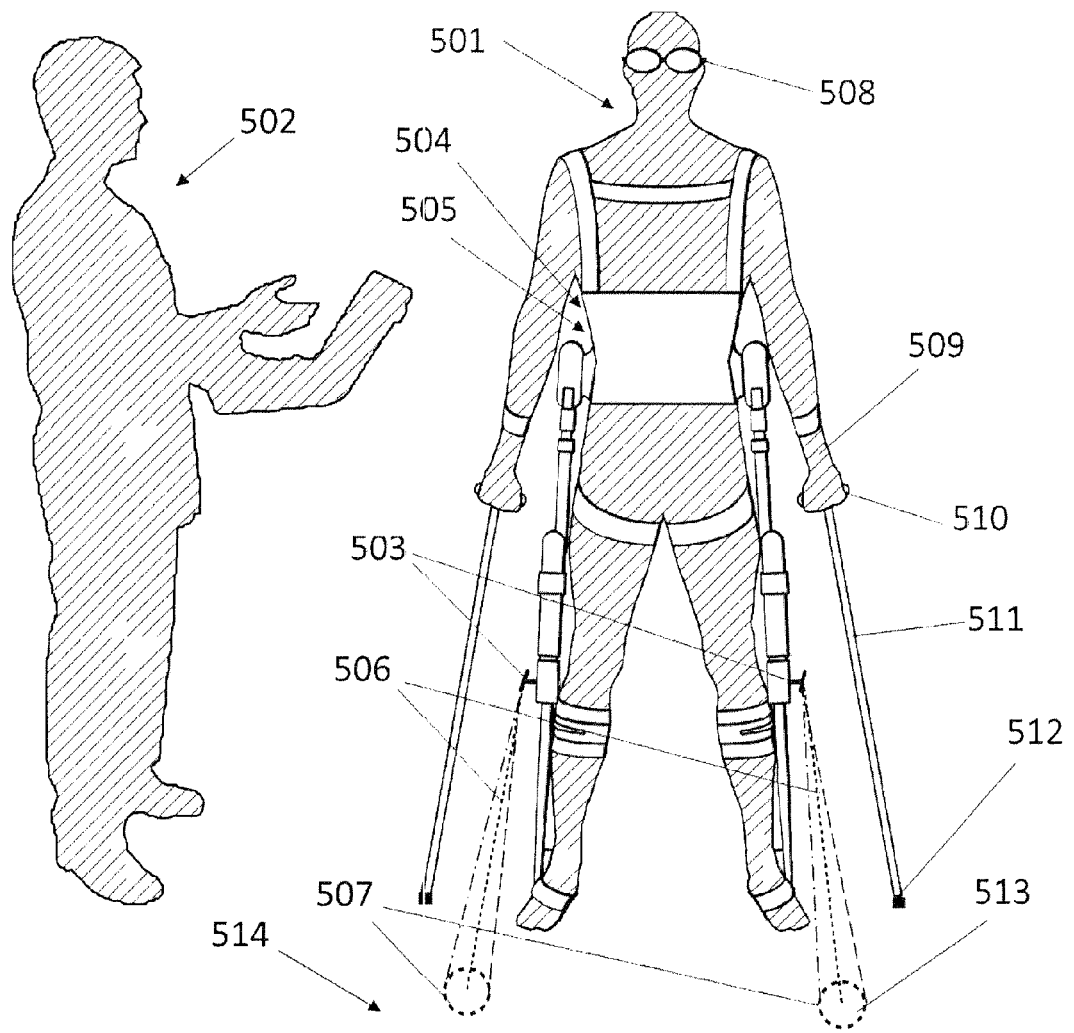
FIG. 5 is a drawing representing a fourth embodiment that shows an ambulatory exoskeleton with an integral projected lights producing placement targets only highly visible to the exoskeleton wearer, who is also wearing special glasses with an optical filter.

With reference to FIG. 5, patient 501 is wearing exoskeleton 504, which is controlled by exoskeleton control system 505. Bystander 502 in the vicinity of exoskeleton 504 and patient 501, and is able to observe patient 501 and exoskeleton 504. Plurality of integral lighting projection means connected to articulated means controlling pan and tilt, 503, is mounted upon the structure of exoskeleton 504 and is in communication with exoskeleton control system 505. Lighting means 503 projects a plurality of colored lighting means that sum to white light, 506, onto support surface 514, resulting in crutch placement targets 507 on support surface 514. Patient 501 wears glasses with an optical filter 508, glasses with an optical filter 508 filter and remove one of the colors projected, making targets 507 a visible colored light to patient 501, while targets 507 appear only as subtle white light to bystander 502 who is not wearing glasses with optical filters 508. Specifically, patient 501 uses hand 509 to grip crutch handle 510 to guide crutch 511, which has ground interacting tip 512, in such a way as to place ground interacting tip 512 upon specific crutch placement target 513.

In one example of the fourth embodiment, a patient is wearing and operating an exoskeleton outside of a rehabilitation setting, such as in a public place. Outside of a rehabilitation setting, both the moving and fixed obstacles faced by an exoskeleton wearer are increased, resulting in greater difficulties in operating the exoskeleton. The use of crutch placement targets, projected by a plurality of lighting means mounted upon the exoskeleton structure by articulated means and controlled by the exoskeleton control system, greatly assists the patient in the operation of the exoskeleton in this setting. However, the projection of visible crutch targets may prove distracting for bystanders, or embarrassing for the patient. The requirement of glasses with an optical filter in order to see these crutch placement targets overcomes these problems, as placement targets will be invisible to bystanders who are not wearing the glasses, allowing for easier exoskeleton use by the patient in a setting outside of rehabilitation.

In a fifth embodiment, the visual feedback system comprises of glasses worn by the exoskeleton wearer with an integrated display system and a camera system, with the glasses displaying placement targets that result in a "heads-up display" to the exoskeleton wearer. The glasses and the cameras are in communication with the exoskeleton control system, and the exoskeleton control system determines the position of the position of the exoskeleton through the plurality of sensors integral to the exoskeleton system that determine exoskeleton pose, while the position of the glasses relative to the exoskeleton system is determined by comparing inertial sensors mounted within the exoskeleton system and inertial sensors mounted within the glasses with integral displays. Such glasses have been developed by companies such as Google with their "Google Glasses" which are currently available.

The position of the glasses with internal displays relative to the exoskeleton system can be determined by comparing inertial sensors such as inertial measurement units mounted within the exoskeleton system and inertial sensors mounted within the glasses with integral displays. Additionally, because the useful information desired to be displayed in often desired to be displayed on the ground, the addition of infrared lights to the exoskeleton feet would improve the foot placement and crutch placement accuracies. The exoskeleton control system could project positions relative to the position of the infrared light. Furthermore, this might act as an ideal trigger to turn on foot and crutch placement displays: When the exoskeleton user looks downward towards their feet the camera in the glasses senses the infrared light on the exoskeleton feet and displays a placement trigger on the ground relative to the location of the infrared light as seen in the camera mounted in the glasses. As the exoskeleton user moves their head up and the camera can no longer see the infrared lights the trigger display locations could be adjusted using dead reckoning of accelerometers mounted in the display glasses. The display of the trigger could then be slowly faded until the exoskeleton user looks toward the exoskeleton feet again. This avoids one of the primary problems of dead reckoning position sensing; that the position may drift over time. The infrared lights mounted to the exoskeleton feet would allow dead reckoning system to recalibrate to an actual position every time the camera can see the feet.

Additionally, the estimates of exoskeleton pose could be enhanced using information from the glasses by integrating infrared lights into the exoskeleton structure. The camera mounted in the glasses could provide relative position information to the exoskeleton control system whenever the exoskeleton wearer looks at the exoskeleton by calculating the distances between the infrared light sources as seen in the camera in the display glasses.

Figure 6:
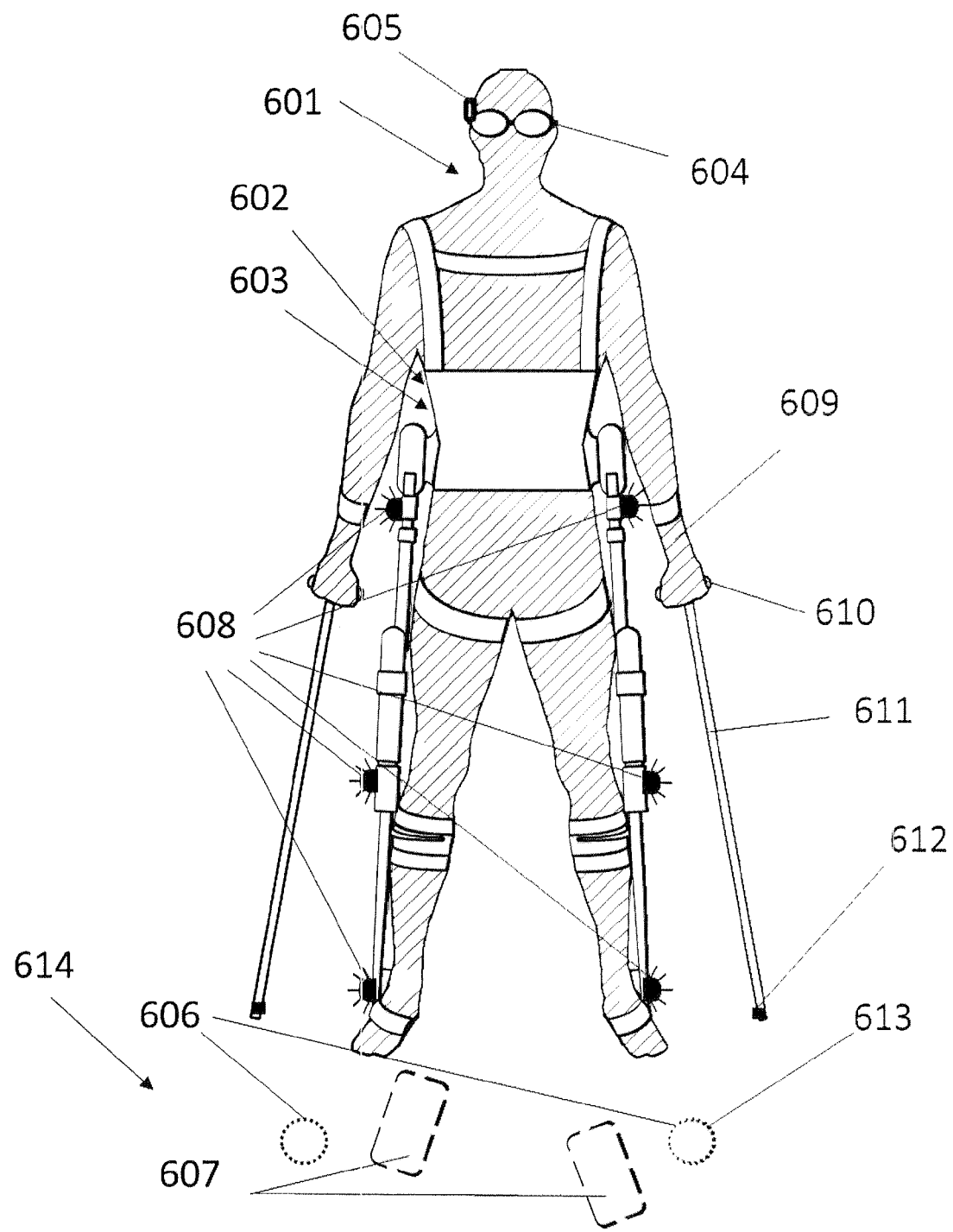
FIG. 6 is a drawing representing a fifth embodiment that shows an ambulatory exoskeleton and an exoskeleton wearer with display glasses that contain and integral camera. The glasses display placement targets and other information to the exoskeleton wearer.

With reference to FIG. 6, patient 601 is wearing exoskeleton 602, which is controlled by exoskeleton control system 603. Patient 601 is also wearing glasses with an integrated display system 604. Upon the glasses with an integrated display system 604 is mounted a camera, 605. Both glasses with an integrated display system 604 and camera 605 are in communication with exoskeleton control system 603. Mounted on various points of exoskeleton structure 602 are infrared lights, 608. Camera 605 observes light emitted from infrared lights 608, and communicates this information to exoskeleton control system 603. Exoskeleton control system 603 uses information from camera 605 to determine the position and direction of glasses with an integrated display system 604 relative to exoskeleton 602, and uses this relative position information to determine the placement of visual images to display in the glasses with an integrated display system 604, including targets for crutch placement, 606, and targets for foot placement 607, with the targets for crutch placement 606 and targets for foot placement 607 being placed on support surface 614. Patient 601 then sees these projected targets 606 and 607 through glasses with an integrated display system 604, and patient 601 then uses these projected targets 606 and 607 to aid in exoskeleton operation. Specifically, patient 601 uses hand 609 to grip crutch handle 610 to guide crutch 611, which has ground interacting tip 612, in such a way as to place ground interacting tip 612 upon specific crutch placement target 613.

In one example of the fifth embodiment, a physical therapist is using an exoskeleton in rehabilitation with a new patient who has no previous experience with exoskeleton therapy. The patient is unfamiliar with various aspects of exoskeleton operation and crutch use. The addition of crutch and foot placement targets displayed in the glasses with and integral display system allows for the patient to more quickly become familiar with crutch and foot placement, shortening the time spent by the learning to use the exoskeleton system, allowing for more rapid use in rehabilitation and greater rehabilitative benefit. In addition to crutch and foot placement targets, these glasses with internal displays could also be used to relay information to the exoskeleton wearer including but not limited to battery level, balance of the exoskeleton system (either center of pressure or center of mass), position of the exoskeleton in a trajectory cycle or group of cycles, movement direction, current action mode, available action modes, error or fault display, or a host of other parameters know by the exoskeleton control system. In addition, a physical therapist might also wear a similar set of glasses with an integrated display system allowing the physical therapist access to similar information from the exoskeleton control system.

Another feedback system involves the communication information on the center of pressure of the exoskeleton and the exoskeleton wearer to the user. Knowledge of the center of pressure is used by a person to feel when they are balanced over their feet. For users without sensation of pressure in their feet, however, this information must be presented by other means. Multiple methods of feedback for the center of pressure are possible. A preferred method is to use tactile feedback at an area where the user is able to feel and process that information.

A sixth embodiment of this invention comprises of a method and device mounted upon and exoskeleton or the exoskeleton wearer that transmits information from the exoskeleton control system to the exoskeleton wearer that provides feedback on the center of pressure of the exoskeleton device and wearer. One embodiment of center of pressure feedback comprises of a wheel that is attached to the exoskeleton or another structure worn by the exoskeleton wearer. The wheel moves in a plane parallel to the exoskeleton wearer's body to indicate center of pressure motion. The wheel can also be actuated to move in and out providing a varying level of pressure. This the pressure can indicate the speed of the center of pressure, the deviation from ideal, or the difference between the center of pressure and the center of mass. In some embodiments, many such wheels in contact with the user so that many different the values can be displayed. In some embodiments, the wheel comprises of a ball and drive by the exoskeleton to move in two dimensions (X-Y) and to push with a varying level of the force, producing a three dimensional display capable of displaying information such as but not limited to a mapping of the exoskeleton wearer's center of pressure in the forward and lateral axis as well as the exoskeleton user's vertical force.

Figure 7:
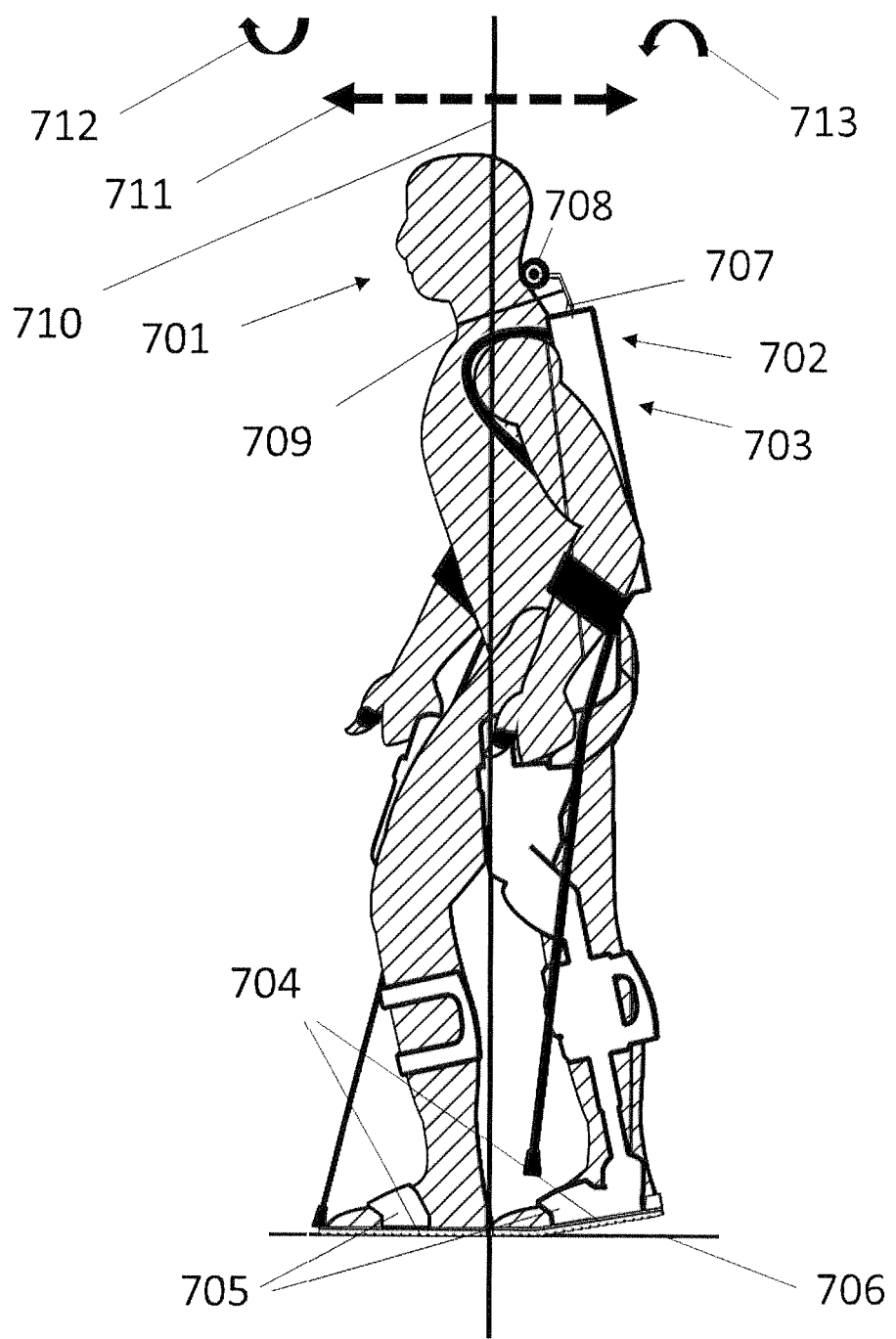
FIG. 7 is a drawing representing a sixth embodiment that shows an ambulatory exoskeleton with a wheel device providing center of pressure feedback to the exoskeleton wearer.

With reference to FIG. 7, patient 701 is wearing exoskeleton 702 which is controlled by exoskeleton control system 703. Attached to exoskeleton 702 are foot structures 705. Foot structures 705 interact with the floor surface, 706. Upon the bottom surface of foot structures 705 are ground force sensors 704 which measures the force by which each foot structure 705 exerts upon the floor 706. Ground force sensors 704 are in communication with exoskeleton control system 703, which uses data from ground force sensors 704 and an algorithm to determine center of pressure for exoskeleton 702 and patient 701, shown in FIG. 7 specifically for the sagittal plane centered at 710. Attached to exoskeleton 702 is a feedback wheel mounting structure 707, which is attached to a motorized wheel 708. Motorized wheel 708 is in contact with patient 701, this contact is aided by the adjustable wheel restraining device 709. Motorized wheel 708 is in communication with exoskeleton control system 703, which can cause motorized wheel 708 to rotate in the sagittal plane either clockwise, 712, or counterclockwise, 713. As exoskeleton control system 703, using data from force sensors 704, detects deflection from the center of pressure in the sagittal plane 710 along dashed line 711, motorized wheel 708 is activated to rotate and provide feedback to patient 701 as to deflection from center of pressure 710. Specifically, if exoskeleton control system 703 detects a forward deflection in center of pressure along 711, then motorized wheel 708 rotates clockwise, 712, providing feedback to patient 701 that they should lean back. Similarly, if exoskeleton control system 703 detects a backwards deflection in center of pressure along 711, then motorized wheel 708 rotates counterclockwise, 713, providing feedback to patient 701 that they should lean forwards.

It will be apparent to one skilled in the art that there are a number of embodiments similar to this seventh embodiment. For example, wheel mounting structure 707 could be actuated and wheel 708 will roll up and down the neck of the person. In this embodiment, the position of the roller communicates information to the wearer. In general, this class of devices controls the motion of a tactile contact point (i.e., the wheel), the position of which communicates information to the person. In some embodiments, the tactile contact point may move in several axes to convey several independent pieces of information to the wearer.

In one example of the sixth embodiment, a patient using an exoskeleton device might have both loss of muscular function in the lower limbs as well as loss of sensation in the lower limbs. Without sensation in the lower limbs, it is difficult for this patient to balance themselves and the exoskeleton device. By placing multiple center of pressure wheels on areas where the patient still has sensation, center of pressure information can be transmitted to the patient restoring a sense of, and aptitude for, balance. In the simple example shown in FIG. 7, one wheel on the back of the neck of the patient provides front to back center of pressure information, as well as a sense of front back balance, to the patient. In another embodiment, the addition of one or more wheel(s) on the side(s) of the neck of the patient might similarly be used to provide side to side center of pressure information (in the coronal plane), and restore a sense of side to side balance to the patient. By combing center of pressure information on front to back and side to side positioning, the overall balance of the patient is improved.

In a seventh embodiment, the center of pressure tactile feedback system comprises of vibratory or other tactile motors that are placed in contact with the exoskeleton wearer's body. The motors are in communication with the exoskeleton control system and apply feedback to the exoskeleton wearer by imparting a pushing feel or a sweep to the direction where the exoskeleton wearer should move. The amplitude of the vibration may indicate information such as the desired speed or degree of motion needed. The vibratory feedback could be given on the torso, arms, neck, or head as is appropriate for the feedback and the exoskeleton wearer's level of injury/impairment. These methods may be combined. For example, one embodiment includes the tactile actuators on the arms of the exoskeleton wearer that are activated to mimic a push left or right as a physical therapist would give during gait training. Likewise, the actuators on the chest and back (or front and back of shoulders) of the exoskeleton wearer would mimic a push forwards or backwards as would be given by a physical therapist. In some embodiments, arrays of vibration motors may be used to produce relative signals across the exoskeleton wearer's body.

Figure 8:
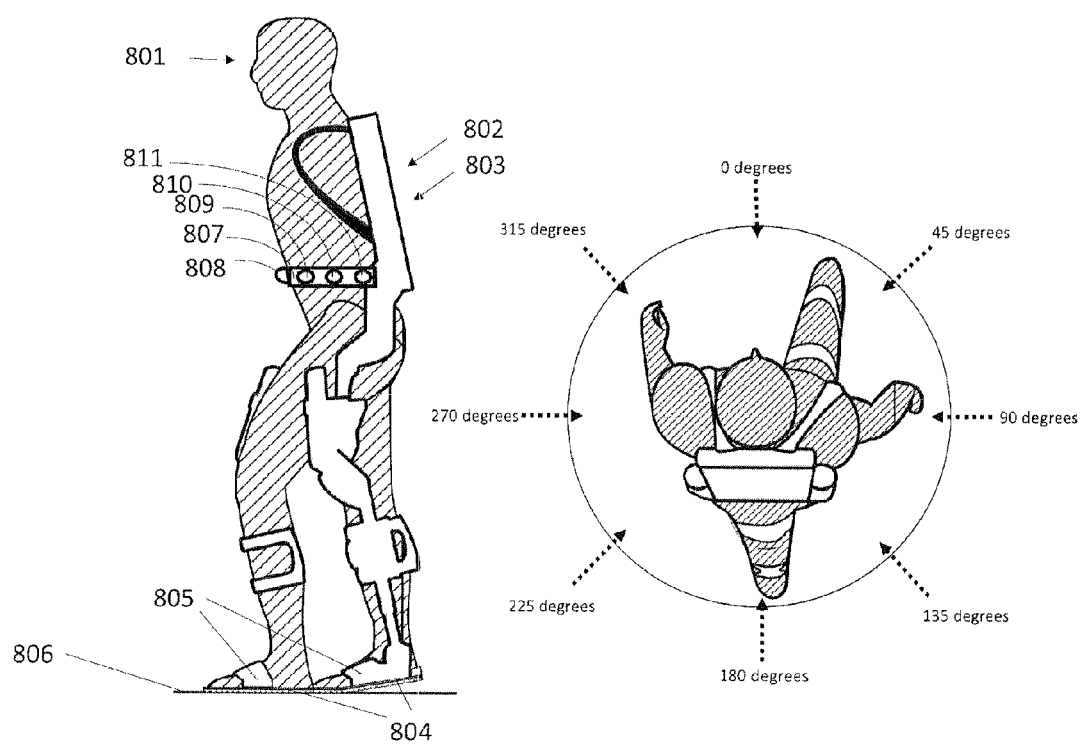
FIG. 8 is a drawing representing a seventh embodiment that shows an ambulatory exoskeleton and an exoskeleton user, with a vibratory belt feedback means attached to either the exoskeleton device or the exoskeleton wearer, with the belt providing center of pressure/balance feedback to the exoskeleton wearer.

With reference to FIG. 8, patient 801 is wearing exoskeleton 802 which is controlled by exoskeleton control system 803. Attached to exoskeleton 802 are foot structures 805. Foot structures 805 interact with the floor surface, 806. Upon the bottom surface of foot structures 805 are ground force sensors 804 which measures the force by which each foot structure 805 exerts upon the floor 806. Ground force sensors 804 are in communication with exoskeleton control system 803, which uses data from ground force sensors 804 and an algorithm to determine center of pressure for exoskeleton 802 and patient 801 in both the sagittal and coronal planes. Patient 801 is wearing feedback belt 807, which is mounted with and controls eight vibratory motors at increments of 45 degrees around its circumference in the axial plane. Specifically shown in the left panel of FIG. 8 are motors at 0 degrees, 808, 315 degrees, 809, 270 degrees, 810, and 225 degrees, 811. Feedback belt 807 is in communication with exoskeleton control system 803 which can activate motors on feedback belt 807 relative to deflection from center of pressure measured by force sensors 804 and determined by exoskeleton control system 803. In a specific example, exoskeleton control system 803 detected a shift in center of pressure towards 300 degrees (300 degrees as shown in FIG. 8), exoskeleton control system 803 would signal feedback belt 807 to activate vibratory motors 810 and 809, while leaving vibratory motors 808 and 811 in the off position. The activation of vibratory motors 810 and 809 would indicate to patient 801 that their center of pressure was drifting towards the two motors 810 and 809 when activated, prompting patient 801 to lean away from these motors 810 and 809.

In one example of the seventh embodiment, a patient using an exoskeleton device might have both loss of muscular function in the lower limbs as well as loss of sensation in the lower limbs. Without sensation in the lower limbs, it is difficult for this patient to balance themselves and the exoskeleton device. By placing multiple vibratory motors on areas where the patient still has sensation, center of pressure information can be transmitted to the patient restoring a sense of, and aptitude for, balance. The eight vibratory motors in the axial plane shown in FIG. 8, which are connected to an exoskeleton control system with center of pressure sensing capabilities, provide a means by which the patient can receive balance feedback in both the sagittal and coronal planes. In this example, if the exoskeleton control system detected that the center of pressure of the patient and exoskeleton was moving too far forward, vibratory motors on the forward portions of the feedback belt would activate and prompt the patient to lean backwards until center of pressure was determined by the exoskeleton control system to be within an acceptable range.

In an eighth embodiment, the center of pressure feedback system comprises of a temperature grid connected to the exoskeleton wearer that is in communication with the exoskeleton control system. The temperature grid conveys information to the exoskeleton wearer by means of inducing sensations of temperature. One embodiment is comprised of a heat grid over the tongue of the exoskeleton wearer. In this embodiment, the surface of the tongue of the exoskeleton wearer is mapped to the base of the feet of the exoskeleton wearer. The center of pressure of the exoskeleton wearer and exoskeleton device is then indicated by heating a node in the same position of the grid as the center of pressure over the foot. The degree of the temperature represents the force at the foot.

In one simplified example of the eighth embodiment, a heat grid is placed on the tongue of an exoskeleton wearer with four heated nodes, one in the front of the tongue, one in the back of the tongue, one of the left of the tongue, and one on the right of the tongue. This heat grid relays center of pressure information from the exoskeleton control system, which is equipped with center of pressure detection means, to the exoskeleton wearer. If the center of pressure of the exoskeleton and exoskeleton wearer shifts forward, the exoskeleton control system activates the heated node on the front of the users tongue, prompting the exoskeleton wearer to lean back. Similarly, if exoskeleton control system detects that the center of pressure is shifting to the left, the heated node on the left of the tongue is activated prompting the exoskeleton wearer to lean right. Center of pressure information in both sagittal and coronal planes could be combined, for example if the exoskeleton control system detected a center of pressure shift back and to the right, the heated nodes at the front and at the right of the tongue would be activated, prompting the exoskeleton wearer to lean forward and to the left.

It should be noted that much more complicated systems could be utilized, including but not limited to grids with many more heated nodes, grids with variable intensities of heat at each node, grids with gradients of heat over node arrays, nodes with pulses of heat, or grids utilizing other feedback over the tongue grid such as vibrotactile, electrical, or other means of stimulation, as well as grids placed in other locations on the exoskeleton wearer's body.

In a ninth embodiment, the center of pressure feedback system is comprised of an auditory device mounted upon the exoskeleton or the exoskeleton wearer that conveys information from the exoskeleton control system to the exoskeleton wearer by sound. The auditory device is comprised of an array of speakers, and the device indicates to the exoskeleton wearer the direction and magnitude of deviation from center of the center of pressure. In one embodiment, as the exoskeleton control system determines that the center of pressure of the exoskeleton and exoskeleton wearer shifts too far to the left, the speakers would generate increasingly louder sound on left of the exoskeleton wearer. Similarly, as the exoskeleton control system determines that the center of pressure of the exoskeleton and exoskeleton wearer shifts too far to the right, the speakers would generate increasingly louder sound on right of the exoskeleton wearer. In another embodiment, the speaker array may simply be comprised of two speakers that are used to give side-to-side or front to back information in this manner. In another embodiment, the addition of more the speakers to the speaker array results in the ability for more precise position information can be transmitted from the exoskeleton control system to the exoskeleton wearer, which is of particular utility in conveying front-to-back position information to the exoskeleton wearer. In another embodiment, one or more the speakers with a variety of tones could be used to indicate to the exoskeleton wearer the direction and magnitude of deviation from center of pressure. In another embodiment, one or more the speakers are used to continuously vary frequency as a function of lateral position so as to convey center of pressure information to the exoskeleton wearer. In another embodiment, one or more the speakers with a variety of tones could be used to indicate direction and magnitude of the position information. It is also possible for one or more speakers to continuously vary its frequency as a function of lateral position so as to convey center of pressure information. In another embodiment, the speaker could emit a series of clicks, with the frequency of the clicks indicating lean angle similar (i.e., the rate of clicks proportional to lean angle) to the way that a geiger counter conveys information through a series of clicks. In another embodiment, by combining two (or more) means of modulating the speakers, the auditory device could convey more than one quantity at a time—for example, the relative left/right volume could indicate left/right lean angle and the frequency could indicate front to back lean angle. Although in this example we discuss center of pressure and lean angle, these are intended as examples, and could be many of the types of information that the machine may wish to convey to the user. Furthermore, the conversion between the information that the machine is communicating to the means by which it is communicated (e.g., the conversion from lean angle to frequency) need not be linear. So while it is possible that $$\text{Frequency} = a \times \text{LeanAngle} + b$$

where $a,b$ are constant
Another embodiment could be $$\text{Frequency} = a \times \sin(LeanAngle) + b$$

or $$\text{Frequency} = a \times \text{sign}(LeanAngle) \times \sqrt{\text{abs}(LeanAngle)} + b$$

Where the last function has the advantage of producing very large changes for values of LeanAngle near zero, but becomes less sensitive at larger values of LeanAngle so that the exoskeleton wearer could most easily find the vertical position (LeanAngle is assumed here to be zero near vertical and could be as simple as the torso angle with respect to gravity or as complex as the angle of a line from the users ankle pivot to their center of mass). The constant term b needs to be chosen so that the equation would not output a negative value for ranges of LeanAngle of interest (since negative frequency makes no physical sense in this context). In practice, it may be desirable for b to be a frequency that is in the middle of a patients hearing range. In some embodiments, these parameters and the equation itself could be adjusted for different exoskeleton wearer to maximize their ability to understand. It should be noted that in the case of stroke patients there may be significant differences in hearing in the affected and unaffected sides of the body, making it of great utility to be able to adjust parameters of the auditory feedback in such a way as to be more readily interpretable to these patients.

Figure 9:
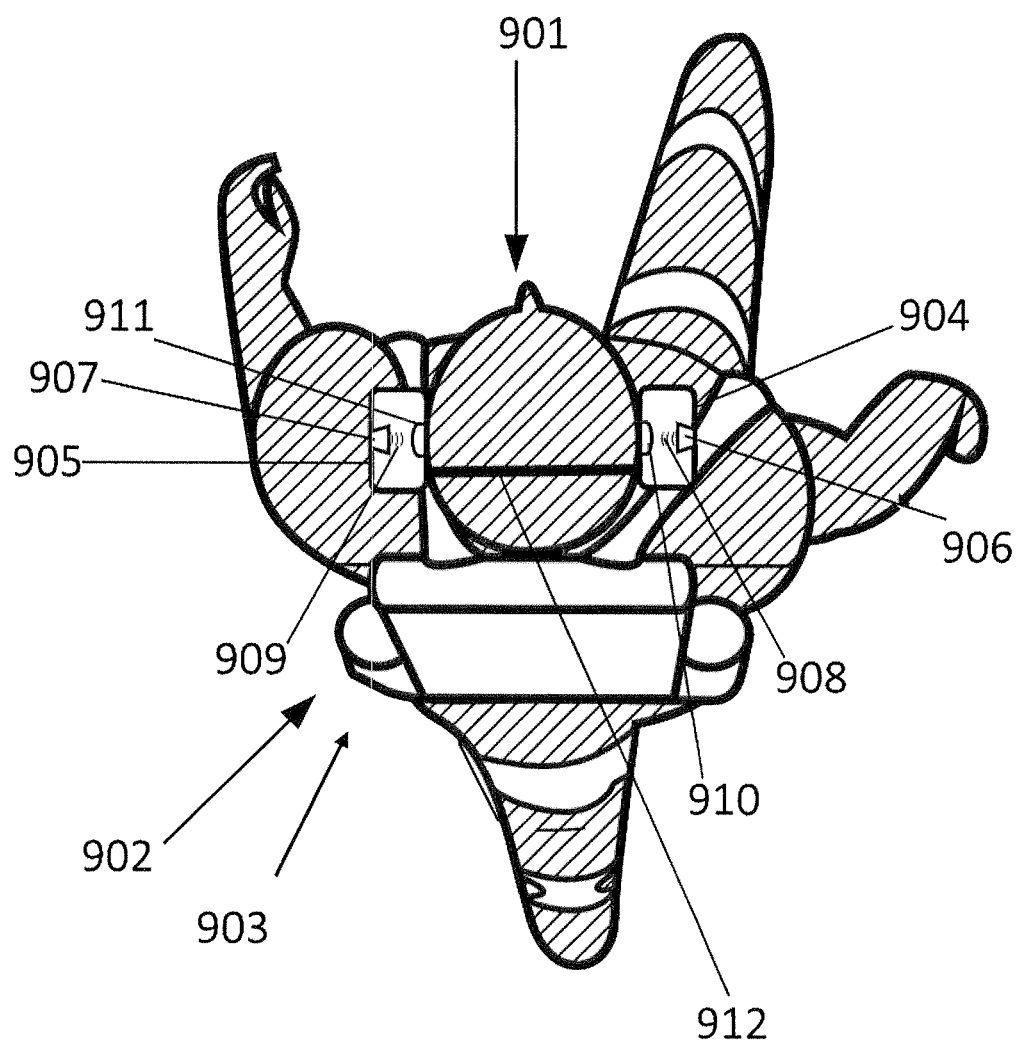
FIG. 9 is a drawing representing a ninth embodiment that shows an ambulatory exoskeleton and an exoskeleton user, with an auditory feedback means attached to either the exoskeleton device or the exoskeleton wearer, with the auditory feedback means providing center of pressure/balance feedback to the exoskeleton wearer.

With reference to FIG. 9, patient 901 is wearing exoskeleton 902 which is controlled by exoskeleton control system 903, with exoskeleton control system 903 being equipped with center of pressure detection means (as shown in FIGS. 6-8). Attached to patient 901 is auditory device retaining strap 912, which is attached to right auditory device 904 and left auditory device 905. Right auditory device 904 contains right speaker 906, which is in communication with exoskeleton control system 903. Right speaker 906 emits sound, 908, based on commands from exoskeleton control system 903, which are heard by the right ear, 910, of patient 901. Left auditory device 905 contains left speaker 907, which is in communication with exoskeleton control system 903. Left speaker 907 emits sound, 909, based on commands from exoskeleton control system 903, which are heard by the left ear, 910, of patient 901. As exoskeleton control system 903 determines a shift of center of pressure along the coronal plane, a signal is transmitted to right auditory device 904 and left auditory device 905. Auditory devices 904 and 905 then cause speakers 906 and 907, respectively, to produce sound 906 and 907, which are heard by patient 901's right ear 910 and left ear 911, respectively.

In one example of the ninth embodiment, a patient using an exoskeleton device might have both loss of muscular function in the lower limbs as well as loss of sensation in the lower limbs. Without sensation in the lower limbs, it is difficult for this patient to balance themselves and the exoskeleton device. Speakers controlled by the exoskeleton control system, which is in communication with the speakers and equipped with center of pressure detection means, allow for sound to be used to convey center of pressure information to the patient, which can improve the balance of the patient wearing the exoskeleton device. In one simplified example, a patient wears an auditory device with left and right speakers that transmit sound to the left and right ears of the patient. As the exoskeleton control system senses that the patient has shifted center of pressure too far to the left, the left speaker produces an audible chance prompting the patient to lean to the right. Similarly, as the exoskeleton control system senses that the patient has shifted center of pressure too far to the right, the right speaker produces an audible chance prompting the patient to lean to the left.

As auditory feedback of the center of pressure may become overwhelming for users, the auditory feedback can also be used to feedback other cues for walking and balancing. One such cue is the lateral shift required before taking a step with the opposite leg. In order to stay balanced while walking, the weight has to shift over the stance leg. Therefore, the auditory feedback can provide cues as to how far the user is from achieving the lateral shift required to balance on the stance leg. Likewise, the forward shift of the hips over the stance foot could also be indicated by auditory feedback.

A tenth embodiment of this invention comprises of a device attached to a walk aid attached to or to the exoskeleton wearer that conveys information from the exoskeleton control system to the exoskeleton wearer that provides feedback and guidance to the exoskeleton wearer in regards to the use of the walk aid. In one embodiment, the walk aid comprises of a crutch held in each hand of the exoskeleton wearer. The crutch handles are equipped with a vibratory motor that is in controlled by the exoskeleton control system. During the walking process, as the exoskeleton wearer shifts their weight, the crutch handle provides vibratory feedback as to where and to what extent the exoskeleton wearer should shift weight. This device is helpful to ensure that the exoskeleton wearer is balanced over their feet rather than relying overly on the walk aid for balance. These methods of feedback used for giving the user information about center of pressure can also be used to give the user information about their overall positioning, such as the location of their hip over the stance foot or their forward and lateral lean. These feedback mechanisms could indicate a need to shift forward/backward or left/right as necessary to achieve a desired orientation. In another embodiment the feedback mechanism in the crutch handle is electrostatic haptic or other any other haptic feedback mechanism.

Figure 10:
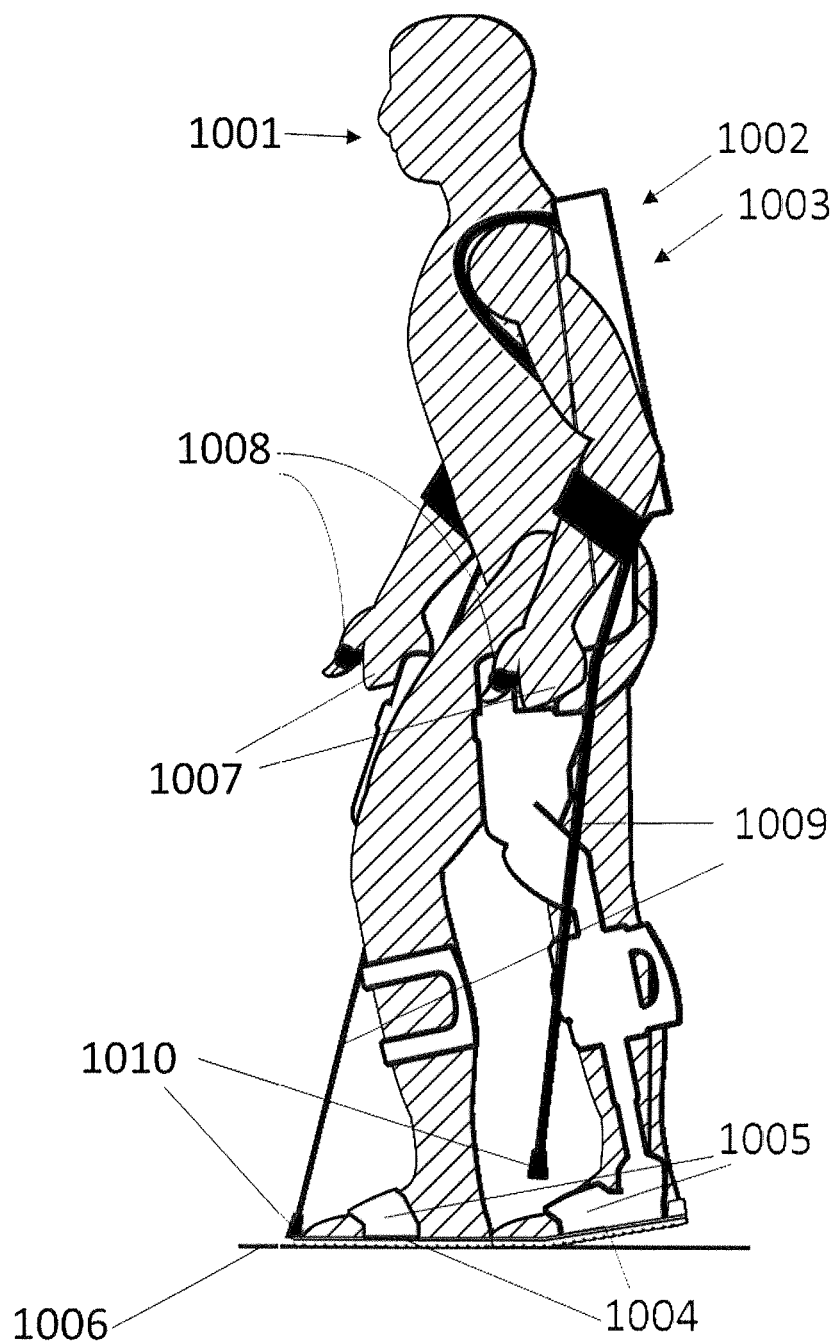
FIG. 10 is a drawing representing a tenth embodiment that shows an ambulatory exoskeleton and an exoskeleton user, with a crutch-integrated feedback means held by the exoskeleton user that provides feedback to the exoskeleton user.

With reference to FIG. 10, patient 1001 is wearing exoskeleton 1002 which is controlled by exoskeleton control system 1003. Attached to exoskeleton 1002 are foot structures 1005. Foot structures 1005 interacts with the floor surface, 1006. Upon the bottom surface of foot structures 1005 are ground force sensors 1004 which measures the force by which each foot structure 1005 exerts upon the floor 1006. Ground force sensors 1004 are in communication with exoskeleton control system 1003, which uses data from ground force sensors 1004 and an algorithm to determine center of pressure for exoskeleton 1002 and patient 1001. Patient 1001 holds crutches 1009 by crutch handles equipped with a vibratory motor, 1008, with crutch handles equipped with a vibratory motor 1008 in communication with exoskeleton control system 1003. Crutches 1009 have a ground interacting tip equipped with a pressure sensor, 1010, with ground interacting tip equipped with a pressure sensor 1010 in communication with exoskeleton control system 1003. Exoskeleton control system 1010 uses an algorithm to process information from ground interacting tip equipped with a pressure sensor 1010, and based on information from both ground force sensors 1004 and ground interacting tip equipped with a pressure sensor 1010 exoskeleton control system determines information on center of pressure and other balance parameters. Exoskeleton control system 1003 then relays guidance and balance shift information to exoskeleton wearer 1001 through crutch handles equipped with a vibratory motor 1008.

In one example of the tenth embodiment, a patient using an exoskeleton device might have both loss of muscular function in the lower limbs as well as loss of sensation in the lower limbs. Without sensation in the lower limbs, it is difficult for this patient to balance themselves and the exoskeleton device. By use providing feedback to the patient through vibratory motors in the walk aid, the exoskeleton control system can decrease ratio of the patient's weight supported by crutches relative to weight supported by the exoskeleton. In addition, this feedback through vibratory motors in the crutches can improve the patient's overall balance, aiding in the course of rehabilitation.

Figure 11:
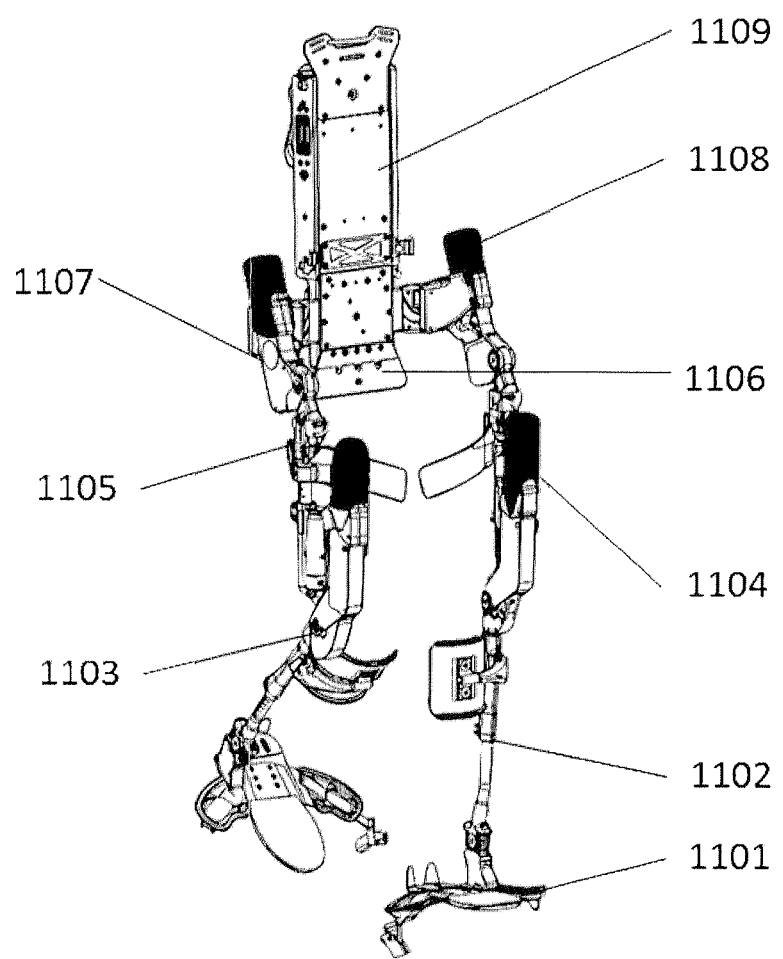
FIG. 11 is a drawing of an ambulatory exoskeleton with specific locations that may be used in any embodiment or combination of embodiments for the additional placement of devices encompassed in any embodiment, including but not limited to lighting means, sensors, or laser pointers.

In addition to the locations previously described for the components in each embodiment by which feedback is provided from the exoskeleton control system to either the exoskeleton user or a physical therapist, or sensors/lighting/other means or systems which are used by the exoskeleton control system to collect data related to the feedback, it should be noted that additional placement locations are possible for the various embodiments of feedback means, sensor means, or lighting means. It should also be noted that multiple embodiments of feedback means may be combined. Some examples of the primary placement options for feedback means and/or related systems are shown in FIG. 11. Location 1101 comprises of feedback means and/or related systems mounted to the structure of the feet, location 1102 comprises of feedback means and/or related systems mounted along the shank (shin), location 1103 comprises of feedback means and/or related systems mounted at the knee joint, location 1104 comprises of feedback means and/or related systems mounted along the knee motor housing, location 1105 comprises of feedback means and/or related systems mounted along the thigh, location 1106 comprises of feedback means and/or related systems mounted to the sacral structure, location 1107 comprises of feedback means and/or related systems mounted at the hip joint, location 1108 comprises of feedback means and/or related systems mounted to the hip motor housing, and location 1109 comprises of feedback means and/or related systems mounted to the torso structure. These specified locations constitute examples of mounting locations only; in no way does this list of locations limit or in any way preclude or restrict the placement of feedback means and/or related systems in alternative positions.

There are various embodiments that convert exoskeleton data into a "feedback ready" format suitable for communication to an exoskeleton operator. These concepts were evaluated based upon the utility of the information communicated to the exoskeleton operator. In particular, it is important to communicate information to the wearer or operator that is not readily apparent to them. Forces applied by the exoskeleton are difficult for a therapist to see, for example, but the angles of various leg segments are very visible. On the other hand, for the wearer of the device, the angles of the leg segments may not be visible, and it may be helpful to relay some information to them (especially if the gait of the orthosis may be irregular). The first set of "feedback ready" algorithms utilize information directly from an exoskeleton's various integral sensors that collect data on the exoskeleton state, including but not limited to joint angles and joint torques.

Algorithms that calculate current exoskeleton joint torque relative to the maximum available exoskeleton joint torque have been identified as important novel "feedback ready" triggers to communicate to an exoskeleton operator. These algorithms and the sensors required are readily apparent to a person skilled in the art of exoskeleton design. When joint torque information is communicated to an exoskeleton wearer, an exoskeleton wearer is given a sense which is a corollary to a human's muscle strain sense. This information enables the wearer to better understand an exoskeleton's limits in the same way a person has an understanding of the limits of their own body. This understanding gives the exoskeleton wearer greater confidence when pushing an exoskeleton device near torque limits and the ability to understand where the limits are.

Concepts have also been developed that are variations on joint torque algorithms. One of these other novel "feedback ready" triggers is the expected joint torque minus the actual joint torque provided. The expected joint torque can be approximately calculated based on the exoskeleton wearer's weight and exoskeleton device pose; methods of making this calculation are readily apparent to a person skilled in the art of exoskeleton design. When communicated to the exoskeleton wearer, this expected minus actual torque information provides the exoskeleton wearer with the ability to immediately sense obstacles that are impeding the exoskeleton's movement. Primarily an object on which the exoskeleton is caught can be sensed and enable the exoskeleton wearer to change course rather than build up torque until the exoskeleton bursts free potentially resulting in damage to the exoskeleton or injury to the exoskeleton wearer.

Another novel "feedback ready" trigger related to joint torque is the interaction forces between the exoskeleton and the exoskeleton operator. This force can be measured using common strain gauges or pressure sensors at human-exoskeleton interface points. Communication of this information to the exoskeleton operator enables similar advantages to that of directly communicating joint torque.

Another novel "feedback ready" trigger related to joint torque is the assistance level provided by the device when a device is used in rehabilitative training. Calculation of assistance level is a function of the interaction forces between the exoskeleton and the exoskeleton wearer and is readily apparent to a person skilled in the art of exoskeleton design. This assistance level enables a physical therapist or a rehabilitation patient to understand how much work the machine is doing and how much work the patient is doing. This gives the physical therapist and the patient the target of minimizing the assistance level to maximize rehabilitative benefit. This is especially applicable in rehabilitative gait training for muscle disorders in which the goal is to improve function when the patient is not using the exoskeleton; in this setting this trigger gives the exoskeleton wearer direct feedback as to how much the exoskeleton is modifying their movements and therefore an idea of what their movements would be like without the assistance of an exoskeleton.

If this joint torque based information is communicated to a physical therapist using an exoskeleton device in a rehabilitation setting, it will give the physical therapist an improved understanding of the exoskeleton's effect on the patient. This understanding will enable the physical therapist to make better decisions about a patient's progression and the exoskeleton device settings required for maximum rehabilitative benefit.

Another class of "feedback ready" triggers are based on exoskeleton and exoskeleton wearer pose information such as center of pressure location, center of gravity location, and relative exoskeleton segment positions. When used with sensory deficient patients such as spinal cord injury patients these triggers attempt to replace the exoskeleton wearer's kinesthetic or somatosensory sense to restore proper proprioception. These embodiments include the positions of the joints relative to each other, which can enable the exoskeleton wearer to understand their position in space more accurately. For example, the feedback may provide the exoskeleton wearer with information concerning their hip extension angle or the distance of the hip to the ankle. These may be qualitative feedback such as "forward" or "back" or may be quantitative indicating the actual distance forward or back.

In an exoskeleton, center of pressure can be calculated using force or pressure sensors located under the feet of the exoskeleton wearer or exoskeleton device (in the case of an exoskeleton with feet). Center of mass can be calculated using joint angle sensors, the exoskeleton, and the exoskeleton wearer's segment weights. In order to improve the accuracy of these the calculations, the joint angles should be corrected based on the flex of the exoskeleton structure using strain gauges embedded within the exoskeleton structure. Relative exoskeleton segment positions can also be calculated using joint angles, segment lengths and flex corrections.

One novel "feedback ready" trigger in the center of pressure class is the relative position of the center of pressure and center of mass of the exoskeleton and exoskeleton wearer system. This "feedback ready" trigger signifies which direction in which the system is falling and can also be used to indicate the speed of the fall by the distance between the center of pressure and the center of mass. This enables the exoskeleton wearer to directly sense their dynamic stability which, in an able-bodied individual, is communicated a combination of their somatosensory sense on their feet and their kinesthetic sense in their lower body.

Another novel "feedback ready" trigger useful with a lower body exoskeletons is the height of each foot from the ground. This trigger acts to restore an exoskeleton wearer's kinesthetic sense. This feedback can be sensed in a variety of manners which are evident to those skilled in the art. One embodiment utilizes proximity sensors, such as sonar emitters and receivers, to calculate the distance to the ground in conjunction with pressure sensors to determine contact. Alternate embodiments may include cameras or laser distance measurements.

Another novel "feedback ready" trigger useful with lower body exoskeletons is the distance from the front of each foot to the closest obstacle. This trigger allows an exoskeleton wearer to sense if it is safe to proceed with a given action. The information fed back to the exoskeleton wearer may include the distance to the obstacle or simply the presence of an obstacle in a given range of the path.

Another novel "feedback ready" trigger useful with lower body exoskeletons is the predicted end effector positions of a selected action. This trigger both provides an exoskeleton wearer with information about an action about to be performed, but also a training target to aim for in order to complete the action. In one embodiment of this method, a visual display, either by a projected point or a heads-up display informs the exoskeleton wearer of the end position of their foot after the action is performed. In an alternate embodiment, the visual display may indicate where to put a crutch or other walk aid in order to prepare for a step.

Another class of "feedback ready" triggers communicates the control system parameters including current actions, planned actions, and control changes to the exoskeleton wearer. These triggers provide the exoskeleton wearer with an improved understanding of the status of the exoskeleton control system so that the exoskeleton wearer is always aware of exoskeleton actions before they are carried out. These triggers need to be communicated in a non-impeding fashion. This communication of parameter changes or actions also provides the exoskeleton wearer the opportunity to confirm or acknowledge the changes if necessary.

Additional "feedback ready" triggers were conceptualized including hand to walking aid force vectors, walking aid to ground forces, torso forward and back angle, torso side to side angle, joint angles, compass heading, mode change requests, mode change confirmations, action initiation, action completion, alerts to unstable positions, and conditional based on functions of individual triggers.

A number of novel feedback systems were also developed using the feedback triggers described above in conjunction with novel means of providing feedback to an exoskeleton wearer's visual, haptic, auditory and thermal sensory pathways. While not all of the devices and methods described herein have been prototyped and functionally tested, the required constituent sensors, controls, and output interfaces that would be required as components of these devices are readily apparent to a person skilled in the art of exoskeleton control.

In all embodiments, the communication means between the exoskeleton sensors and the exoskeleton control system can either be wireless or hardwired. Similarly, the communication means between the feedback systems and the exoskeleton system can either be wireless or hardwired.

Figure 12:
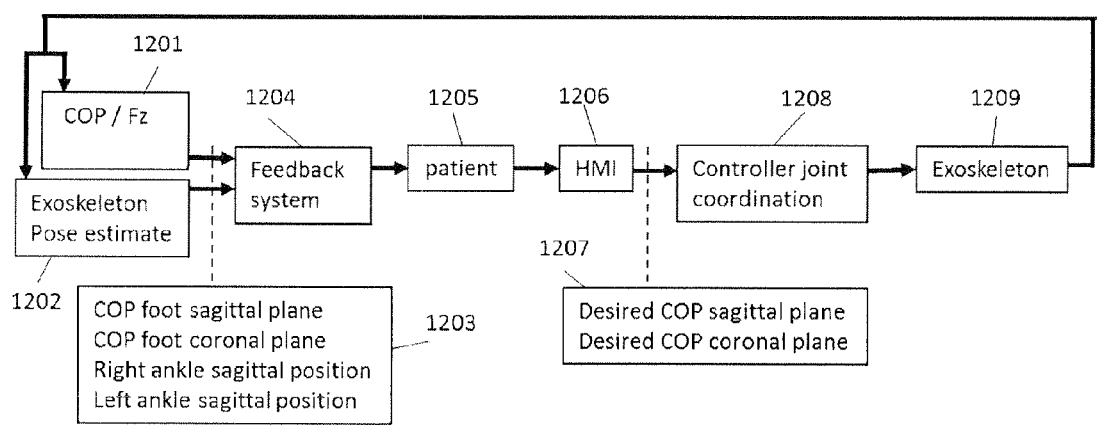
FIG. 12 is a control loop schematic showing an exoskeleton controller based on feeding information to and from the person wearing an exoskeleton device.

It is important to understand that the methods and devices disclosed here, in combination with our disclosures in other applications relating to reading human intentions into the machine, could be used to build an exoskeleton system where the patient themselves closes the highest control "loop." In this embodiment, the methods disclosed in this application could, for example, be used to communicate the center of pressure of the user/machine system to the patient and then the patient could, in methods disclosed in our other applications, indicate how they want the machine to move in real time by moving their gait aids (or fingers, or, hands, or anus, or head to name a few more embodiments). As a result, the patient, who may have both motor and sensory impairments, and possibly complete impairment of both in their legs, could regain a normal gait over which they have complete control. The patient could control the machine to balance by moving their gait aids to indicated a desired center of pressure position, and instruct the machine to take a step by requesting a center of pressure position in front of the feet, or behind the feet to walk backwards. FIG. 12 includes a control system block diagram that shows this embodiment.

In regards to FIG. 12, Center of Pressure and Force 1201 is the center of pressure of force distributed over the support surface, and "Fz," the vertical force of the human and machine on the support surface. Exoskeleton pose estimate 1202 is the exoskeletons internal representation of its orientation in space. Data from both 1201 and 1202, collectively containing information on 1203, which include center of pressure information in both sagittal and coronal planes as well as ankle positions in the sagittal plane, is relayed to feedback system 1204 which continuously transfers information from the patient wearing the exoskeleton device, 1205, to the machine such as those disclosed in this application. Patient 1205 uses human machine interface 1206, a system that continuously transfers information from the person to the machine such as those disclosed in our other applications, to convey information of patient 1205's intent, including the desired center of pressure in both the sagittal and coronal planes, 1207, to controller joint coordination module 1208, which is the lower level machine control done in the exoskeleton controller that manipulates the exoskeleton actuators to produce the desired center of pressure position. Closed loop control 1208 commands the exoskeleton device, 1209, resulting in changes in exoskeleton trajectories. Using this system, it becomes possible to close the control loop through the person so that the person may directly command the motion of the exoskeleton. Although methods and interfaces for communicating from the machine to the human have become well known to the art, combining these with the feedback systems disclosed in this application enable the person wearing the device to effectively control the exoskeleton in a way not previously understood.

The invention claimed is:

1. A lower extremity orthosis configured to be coupled to a person, the orthosis comprising:
    a torso link configured to be coupled to a torso of the person,
    at least one leg link configured to be coupled to a leg of the person,
    at least one actuator configured to shift the at least one leg link with respect to the torso link,
    a plurality of sensors configured to measure at least one of an orientation and forces of the orthosis and the person,
    a controller configured to receive signals from the plurality of sensors, estimate at least one feedback ready value based on signals from the plurality of sensors, and control the at least one actuator to assist a gait or movement of the person, and at least one feedback system operated by the controller and configured to communicate the at least one feedback ready value to the person, whereby the orthosis provides the person with orthosis operational information not otherwise available to the person, wherein the at least one feedback system includes at least one of (1) at least one light corresponding to each of the at least one actuator, the at least one light indicating an effort being produced by the orthosis at that corresponding actuator, and (2) a display mounted in a field of view of the person, the display overlaying graphics so that the graphics indicate locations on a support surface.

2. The orthosis of claim 1, wherein the at least one feedback system includes the at least one light corresponding to each of the at least one actuator, the at least one light indicating a joint torque being produced by the orthosis at that corresponding actuator.

3. The orthosis of claim 1, wherein the plurality of sensors includes a force sensor located at an interface point, and the at least one feedback system includes at least one light corresponding to the interface point, the at least one light indicating a force sensed at that interface point.

4. The orthosis of claim 1, wherein the at least one feedback system includes the at least one light corresponding to each of the at least one actuator, and the at least one feedback system includes at least one laser mounted to the orthosis with at least one feedback actuator, the at least one feedback actuator controlled by the controller to point to a location on the support surface.

5. The orthosis of claim 4, further comprising at least one gait aid, wherein the controller estimates an ideal location for a next gait aid placement, and the ideal location is indicated by the at least one laser.

6. The orthosis of claim 5, further including providing an optical filter to the person such that light reflected from the at least one laser hitting the support surface is generally visible only to the person.

7. The orthosis of claim 1, wherein the at least one feedback system includes the display mounted in the field of view of the person, the display overlaying graphics so that the graphics indicate targets for gait aid or foot placement on the support surface.

8. The orthosis of claim 1, wherein the at least one feedback system includes at least one feedback actuator and a tactile contact point in contact with the person and configured to be moved by the at least one feedback actuator, and the at least one feedback actuator is controlled by the controller to convey information to the person.

9. The orthosis of claim 1, wherein the at least one feedback system includes a heat grid controlled by the controller.

10. The orthosis of claim 1, wherein the person uses at least one gait aid, and the at least one feedback system includes a vibratory actuator and is coupled to the at least one gait aid whereby the controller conveys information to the person by the vibratory actuator.

11. The orthosis of claim 1, further comprising a human to machine interface including a signaling device provided to the person, the controller configured to receive signals from the signaling device, whereby the controller incorporates the person as part of a closed loop control of the orthosis, wherein the at least one feedback system provides information to the person on a measured center of pressure, and the human to machine interface provides information to the controller on a center of pressure desired by the person, whereby the person controls motion of the orthosis.

12. A method of operating a lower extremity orthosis including a torso link configured to be coupled to a torso of a person, at least one leg link configured to be coupled to a leg of the person, at least one actuator configured to shift the at least one leg link relative to the torso link, a plurality of sensors configured to measure at least one of an orientation and forces of the orthosis or person, and a feedback system configured to communicate to the person, said method comprising:

controlling the at least one actuator to assist a gait of the person, estimating at least one feedback ready value based on signals from the plurality of sensors, and communicating the at least one feedback ready value to the person with the feedback system in order to provide the person with orthosis operational information not otherwise available to the person, wherein the at least one feedback system includes at least one of (1) at least one light corresponding to each of the at least one actuator, the at least one light indicating an effort being produced by the orthosis at that corresponding actuator, and (2) a display mounted in a field of view of the person, said method further comprising overlaying graphics so that the graphics indicate locations on a support surface.

13. The method of claim 12, wherein the feedback system includes the at least one light corresponding to each of the at least one actuator, said method further comprising: indicating a joint torque being produced by the orthosis at the corresponding said actuator.

14. The method of claim 12, wherein the plurality of sensors includes a force sensor located at an interface point, and the feedback system includes at least one light corresponding to the interface point, said method further comprising: indicating a force, sensed at the interface point, with the at least one light.

15. The method of claim 12, wherein the feedback system includes the at least one light corresponding to each of the at least one actuator, and the feedback system includes at least one laser mounted to the orthosis, said method further comprising: pointing the at least one laser to a location on the support surface.

16. The method of claim 15, further comprising: employing at least one gait aid, and estimating an ideal location for a next gait aid placement, and pointing the at least one laser at the ideal location.

17. The method of claim 16, further comprising: providing an optical filter to the person such that light reflected from the at least one laser hitting the support surface is generally visible only to the person.

18. The method of claim 12, wherein the feedback system includes the display mounted in the field of view of the person, said method further comprising: overlaying graphics so that the graphics indicate targets for gait aid or foot placement on the support surface.

19. The method of claim 12, wherein the feedback system includes at least one feedback actuator and a tactile contact point in contact with the person and configured to be moved by the at least one feedback actuator, said method further comprising: conveying information to the person by moving the tactile contact point.

20. The method of claim 12, further comprising: controlling a heat grid provided as part of the feedback system.

21. The method of claim 12, further comprising:
employing at least one gait aid with use of the orthosis, and
conveying information to the person by a vibratory actuator of the feedback system which is coupled to the at least one gait aid.

22. The method of claim 12, further comprising:
receiving signals from a signaling device of a human-to-machine interface,
incorporating the person as part of a closed loop control of the orthosis through the human-to-machine interface,
providing information to the person on a measured center of pressure, and
accepting a desired center of pressure desired from the person, whereby the person controls motion of the orthosis.

23. A method of controlling a lower extremity orthosis including a torso link configured to be coupled to a torso of a person, at least one leg link configured to be coupled to a leg of the person, at least one actuator configured to shift the at least one leg link with respect to the torso link, a plurality of sensors configured to monitor the orthosis, and at least one light, said method comprising:
receiving signals from the plurality of sensors and controlling the at least one actuator to assist a gait of the person, and
controlling the at least one light to continuously indicate an effort produced by the at least one actuator, whereby the orthosis provides a visual indication of assistance provided by the orthosis.

24. The method of claim 23, further comprising:
providing at least one force sensor configured to produce an estimate of a force between the person and the orthosis, and
continuously indicating the estimate of the force with the at least one light, whereby the orthosis provides a visual indication of the force applied to the person.

25. The method of claim 23, further comprising:
sensing forces produced by the at least one actuator of the orthosis; and
illuminating selective ones of the at least one light in providing a visual indication of the forces provided by the orthosis.

26. The method of claim 23, wherein controlling the at least one light includes controlling the at least one light to continuously indicate a joint torque produced by the at least one actuator.

* * * * *